(12) United States Patent
Jung

(10) Patent No.: US 11,980,479 B2
(45) Date of Patent: May 14, 2024

(54) WEARABLE ELECTRONIC DEVICE AND METHOD FOR DETECTING CONTACT OF LIVING BODY TO WEARABLE ELECTRONIC DEVICE

(71) Applicant: Samsung Electronics Co., Ltd., Gyeonggi-do (KR)

(72) Inventor: Hyunjun Jung, Gyeonggi-do (KR)

(73) Assignee: Samsung Electronics Co., Ltd., Suwon-si (KR)

(*) Notice: Subject to any disclaimer, the term of this patent is extended or adjusted under 35 U.S.C. 154(b) by 273 days.

(21) Appl. No.: 16/952,168

(22) Filed: Nov. 19, 2020

(65) Prior Publication Data
US 2021/0169420 A1 Jun. 10, 2021

(30) Foreign Application Priority Data
Dec. 10, 2019 (KR) .................. 10-2019-0163919

(51) Int. Cl.
*A61B 5/00* (2006.01)
*A61B 5/24* (2021.01)
*A61B 5/024* (2006.01)
*A61B 5/318* (2021.01)

(52) U.S. Cl.
CPC .............. *A61B 5/6843* (2013.01); *A61B 5/24* (2021.01); *A61B 5/681* (2013.01); *A61B 5/742* (2013.01); *A61B 5/7475* (2013.01); *A61B 5/02416* (2013.01); *A61B 5/318* (2021.01)

(58) Field of Classification Search
CPC ......... A61B 5/6843; A61B 5/24; A61B 5/681; A61B 5/742; A61B 5/7475
See application file for complete search history.

(56) References Cited

U.S. PATENT DOCUMENTS

| 10,192,044 B2 | 1/2019 | Choe et al. |
| 2009/0024017 A1 | 1/2009 | Ruffini et al. |
| 2011/0288605 A1* | 11/2011 | Kaib .................... A61B 5/7221 607/5 |

(Continued)

FOREIGN PATENT DOCUMENTS

| JP | 2017-228132 A | 12/2017 |
| KR | 10-2017-0041595 A | 4/2017 |

(Continued)

OTHER PUBLICATIONS

International Search Report dated Apr. 26, 2021.
European Search Report dated Nov. 23, 2022.

*Primary Examiner* — Yingchuan Zhang
*Assistant Examiner* — Laura Hodge
(74) *Attorney, Agent, or Firm* — Cha & Reiter, LLC

(57) ABSTRACT

According to an embodiment, a wearable electronic device may include at least two electrodes for measuring a biometric signal, a living body contact detecting unit configured to apply a voltage to at least one electrode contacting a living body among the at least two electrodes and output information indicating an operation state for biometric signal measurement of the wearable electronic device based on a voltage output from the at least one electrode, and a processor configured to determine the operation state for biometric signal measurement of the wearable electronic device, based on the information received from the living body contact detecting unit. Various other embodiments may be provided.

18 Claims, 19 Drawing Sheets

(56) References Cited

U.S. PATENT DOCUMENTS

| | | | |
|---|---|---|---|
| 2015/0119747 A1* | 4/2015 | Torfs | A61B 5/053 |
| | | | 600/547 |
| 2016/0228064 A1* | 8/2016 | Jung | A61B 5/4872 |
| 2016/0296136 A1* | 10/2016 | Jung | A61B 5/681 |
| 2016/0341600 A1 | 11/2016 | Aloe et al. | |
| 2016/0378965 A1* | 12/2016 | Choe | G06F 1/1626 |
| | | | 726/19 |
| 2017/0049352 A1 | 2/2017 | Mirov | |
| 2017/0100046 A1 | 4/2017 | Roh et al. | |
| 2017/0172452 A1* | 6/2017 | Lee | A61B 5/4875 |
| 2018/0000375 A1* | 1/2018 | Jung | A61B 5/681 |
| 2018/0235542 A1* | 8/2018 | Yun | A61B 5/6843 |
| 2019/0072912 A1* | 3/2019 | Pandya | A61B 5/332 |
| 2019/0320981 A1* | 10/2019 | Kodama | A61B 5/7221 |

FOREIGN PATENT DOCUMENTS

| | | |
|---|---|---|
| KR | 10-2018-0105800 A | 10/2018 |
| WO | 2017/057846 A1 | 4/2017 |

\* cited by examiner

WEARABLE ELECTRONIC DEVICE AND METHOD FOR DETECTING CONTACT OF LIVING BODY TO WEARABLE ELECTRONIC DEVICE

CROSS-REFERENCE TO RELATED APPLICATION(S)

This application is based on and claims priority under 35 U.S.C. 119 to Korean Patent Application No. 10-2019-0163919, filed on Dec. 10, 2019, in the Korean Intellectual Property Office, the disclosure of which is herein incorporated by reference in its entirety.

BACKGROUND

Field

One or more embodiments disclosed herein generally relate to a wearable electronic device capable of detecting contact of a living body portion thereto using electrodes, and a method for detecting contact of the living body to the wearable electronic device.

Description of Related Art

As hardware and software technologies develop, electronic devices supporting various functions are introduced into the market. Recently, increased attention has been directed to healthcare, and this has led to increased demand for measurement and management of health conditions of users of electronic devices. Accordingly, markets have emerged for electronic devices equipped with various biometric sensors for measuring health conditions and for providing related services.

The biometric sensors may include a blood glucose meter, a blood pressure monitor, a thermometer, a heart rate monitor (HRM), an electrocardiogram (ECG) sensor, a photoplethysmography (PPG) sensor, a fingerprint scanner, an iris scanner, and the like.

Among the aforementioned sensors, the ECG sensor may detect a potential difference generated when heart muscle contracts and relaxes via the ECG electrode in contact with the living body skin. The action potential generated by the heartbeat causes a current that spreads from the heart to the whole body, and this current generates a potential difference. The ECG sensor can be used to determine the size of the heartbeat and whether the heart is damaged by detecting the electrical activity of the heart and measuring whether the heartrate is constant. The ECG sensor can be deployed in various applications, such as recognizing the user's emotional state or performing user authentication using a unique ECG value.

Various biometric sensors may be equipped in a wearable electronic device that may be placed on the user. Upon detecting that the device is worn, the wearable electronic device may obtain biometric signals and check the user's health condition.

SUMMARY

A wearable electronic device equipped with various biometric sensors may apply current to two electrodes of the device and detect whether the wearable electronic device is worn on the user's body using the potential between the two electrodes. The method of detecting whether the wearable electronic device is worn on the user's body using the potential between the two electrodes to which current has been applied changes the potential between the two electrodes and thus limits detection of biometric signals. When alternating current (AC) is applied to the two electrodes, unnecessarily high frequency sampling may be required, or an additional analog circuit for extracting the impedance component, e.g., a demodulator, may be needed.

According to certain embodiments, there is provided a wearable electronic device capable of detecting contact of a living body portion thereto using electrodes, and a method for detecting contact of the living body to the wearable electronic device.

In accordance with an embodiment, a wearable electronic device comprises at least two electrodes for measuring a biometric signal, a living body contact detecting unit configured to apply a voltage to at least one electrode contacting a living body among the at least two electrodes and output information indicating an operation state for biometric signal measurement of the wearable electronic device based on a voltage output from the at least one electrode, and a processor configured to determine the operation state for biometric signal measurement of the wearable electronic device, based on the information received from the living body contact detecting unit.

In accordance with an embodiment, a method for detecting contact of a living body to a wearable electronic device comprises applying a voltage to at least one electrode contacting the living body among at least two electrodes for biometric signal measurement, outputting information indicating an operation state for biometric signal measurement of the wearable electronic device based on another voltage output from the at least one electrode, and determining the operation state of the biometric signal measurement of the wearable electronic device based on the information indicating the operation state of the biometric signal measurement of the wearable electronic device.

Other aspects, advantages, and salient features of the disclosure will become apparent to those skilled in the art from the following detailed description, which, taken in conjunction with the annexed drawings, discloses exemplary embodiments of the disclosure.

BRIEF DESCRIPTION OF THE DRAWINGS

A more complete appreciation of the disclosure and many of the attendant aspects thereof will be readily obtained as the same becomes better understood by reference to the following detailed description when considered in connection with the accompanying drawings, wherein.

Throughout the drawings, like reference numerals will be understood to refer to like parts, components, and structures.

DETAILED DESCRIPTION

Figure 1A:
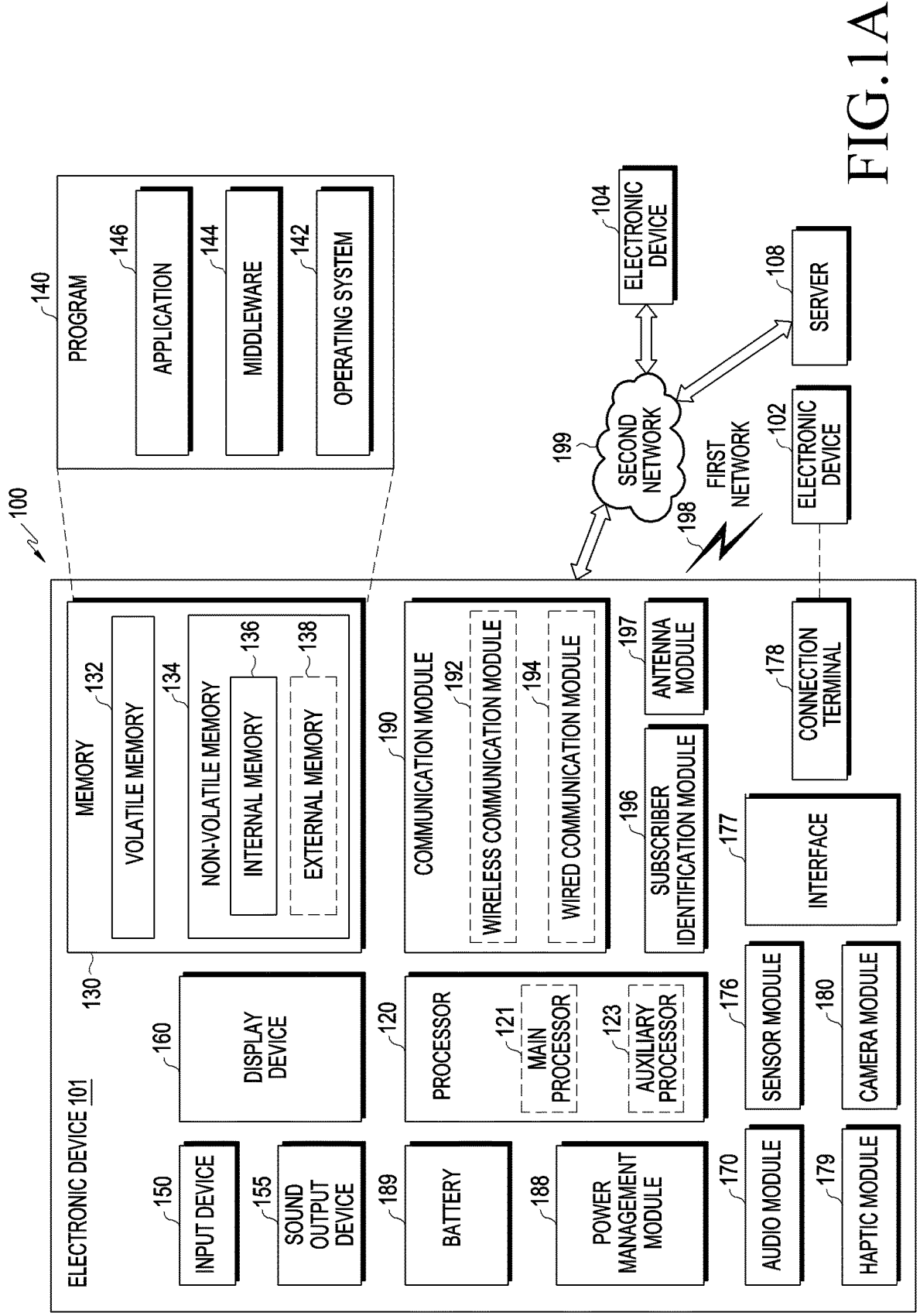
FIG. 1A is a view illustrating an electronic device in a network environment according to an embodiment.

FIG. 1A is a block diagram illustrating an electronic device 101 in a network environment 100a according to various embodiments. Referring to FIG. 1A, the electronic device 101 in the network environment 100a may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by other component (e.g., the processor 120) of the electronic device 101, from the outside (e.g., a user) of the electronic device 101. The input device 150 may include, for example, a microphone, a mouse, a keyboard, or a digital pen (e.g., a stylus pen).

The sound output device 155 may output sound signals to the outside of the electronic device 101. The sound output device 155 may include, for example, a speaker or a receiver. The speaker may be used for general purposes, such as playing multimedia or playing record, and the receiver may be used for an incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or motion) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN))). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device). According to an embodiment, the antenna module may include one antenna including a radiator formed of a conductor or conductive pattern formed on a substrate (e.g., a printed circuit board (PCB)). According to an embodiment, the antenna module 197 may include a plurality of antennas. In this case, at least one antenna appropriate for a communication scheme used in a communication network, such as the first network 198 or the second network 199, may be selected from the plurality of antennas by, e.g., the communication module 190. The signal or the power may then be transmitted or received between the communication module 190 and the external electronic device via the selected at least one antenna. According to an embodiment, other parts (e.g., radio frequency integrated circuit (RFIC)) than the radiator may be further formed as part of the antenna module 197.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. The external electronic devices 102 and 104 each may be a device of the same or a different type from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

Figure 1B:
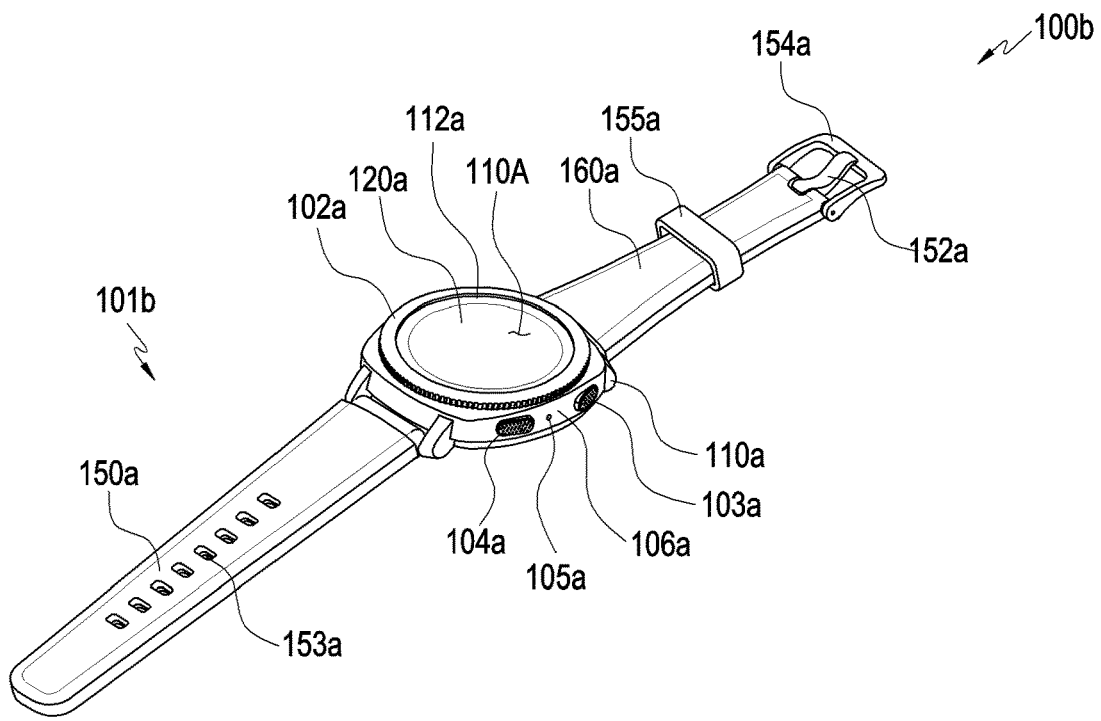
FIG. 1B is a front perspective view illustrating an electronic device according to an embodiment.
Figure 1C:
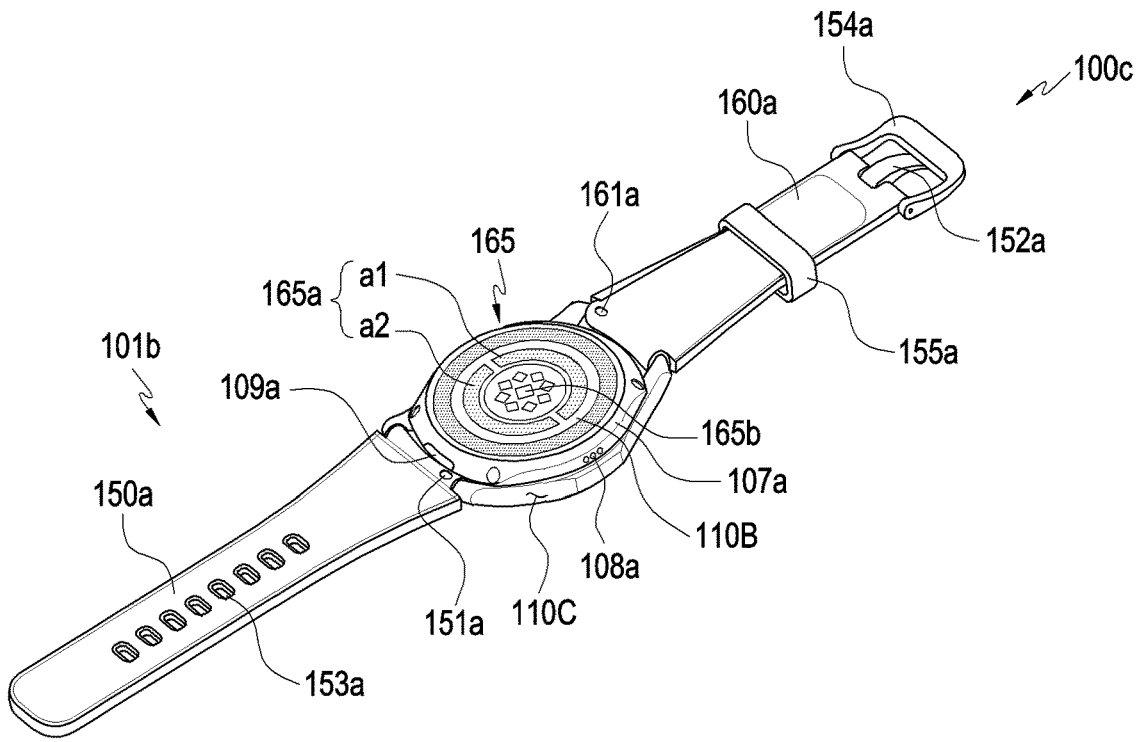
FIG. 1C is a rear perspective view illustrating an electronic device as shown in FIG. 1B.

FIG. 1B is a front perspective view 100b illustrating an electronic device according to an embodiment. FIG. 1C is a rear perspective view 100c illustrating an electronic device as shown in FIG. 1B.

Referring to FIGS. 1B and 1C, according to an embodiment, the wearable device 101b (e.g., the electronic device 101 of FIG. 1A) may include a housing 110a including a first surface (or front surface) 110A, a second surface (or rear surface) 110B, and a side surface 110C surrounding the space between the first surface 110A and the second surface 110B and coupling members 150a and 160a connected to at least part of the housing 110a and configured to allow the electronic device 101b to be detachably worn on the user's body (e.g., his wrist or ankle). According to another embodiment (not shown), the housing may be a structure forming only a part of the first surface 110A, the second surface 110B, and the side surface 110C of FIG. 1. According to an embodiment, at least part of the first surface 110A may have a substantially transparent front plate 112a (e.g., a glass plate or polymer plate including various coat layers). The second surface 110B may be formed of a substantially opaque rear plate 107a. According to an embodiment, when the electronic device 101b includes a sensor module 165 disposed on the second surface 110B, the rear plate 107a may at least partially include a transparent region. The rear plate 107a may be made of, e.g., laminated or colored glass, ceramic, polymer, metal (e.g., aluminum, stainless steel (STS), or magnesium), or a combination of at least two thereof. The side surface 110C may be formed by a side bezel structure (or a "side member" or "bezel") 106a that couples to the front plate 112a and the rear plate 107a and includes metal and/or polymer. According to an embodiment, the rear plate 107a and the side bezel structure 106a may be integrally formed together and include the same material (e.g., metal, such as aluminum). The coupling members 150a and 160a may be made of various materials in various shapes. A uni-body structure or multiple unit links which is flexible may be formed of fabric, leather, rubber, urethane, metal, ceramic, or a combination of at least two thereof.

According to an embodiment, the electronic device 101b may include at least one or more of a display 120a (refer to FIG. 1D), audio modules 105a and 108a, a sensor module 165, key input devices 102a, 103a, and 104a, and a connector hole 109a. According to an embodiment, the electronic device 101b may exclude at least one of the components (e.g., the key input devices 102a, 103a, and 104a, connector hole 109a, or sensor module 165) or may add other components.

According to an embodiment, the electronic device 101b may include a plurality of electrodes for measuring a biometric signal. At least one of the plurality of electrodes may be integrated with at least one of the key input device 102a, 103a, or 104a, the bezel 106a, the display 120a, or the housing 110a. Among the key input devices, the wheel key 102a may include a rotary bezel. The display 120a may be exposed through a substantial portion of, e.g., the front plate 112a. The display 120a may have a shape corresponding to the shape of the front plate 112a, e.g., a circle, ellipse, or polygon. The display 120a may be coupled with, or disposed adjacent to, a touch detection circuit, a pressure sensor capable of measuring the strength (pressure) of touches, and/or fingerprint sensor.

According to an embodiment, the display 120a may include at least one transparent electrode for measuring biometric signals, where the transparent electrode is one of the plurality of electrodes for measuring biometric signals.

The audio modules 105a and 108a may include a microphone hole 105a and a speaker hole 108a. The microphone hole 105a may have a microphone inside to obtain sounds produced outside the electronic device. According to an embodiment, there may be a plurality of microphones to be able to detect the direction of the sound. The speaker hole 108a may be used for an external speaker or a receiver for phone talks. According to an embodiment, a speaker may be included without the speaker hole (e.g., piezo speaker).

The sensor module 165 may generate an electrical signal or data value corresponding to an internal operating state or external environmental state of the electronic device 101b. The sensor module 165, e.g., a biometric sensor module 165 placed on the second surface 110B of the housing 110a, may include an electrocardiogram (ECG) sensor 165a including at least two electrodes a1 and a2 for ECG measurement and a photoplethysmogram (PPG) sensor 165b for heartrate measurement. The electronic device 101b may further include sensor modules not shown, e.g., at least one of a gesture sensor, a gyro sensor, an atmospheric pressure sensor, a magnetic sensor, an acceleration sensor, a grip sensor, a color sensor, an infrared (IR) sensor, a biometric sensor, a temperature sensor, a humidity sensor, or an illuminance sensor.

The key input devices 102a, 103a, and 104a may include a wheel key 102a disposed on the first surface 110A of the housing 110a that is rotatable in at least one direction and/or side key buttons 103a and 104a disposed on the side surface 110C of the housing 110a. The wheel key 102a may have a shape corresponding to the shape of the front plate 112a. According to an embodiment, the electronic device 101b may exclude all or some of the above-mentioned key input devices 102a, 103a, and 104a and the excluded key input devices 102a, 103a, and 104a may be implemented in other forms, e.g., as soft keys on the display 120a. The connector hole 109a may receive a connector (e.g., a universal serial bus (USB) connector) for transmitting and receiving power and/or data to/from an external electronic device. Another connector hole (not shown) may be included for receiving a connector for transmitting and receiving audio signals to/from the external electronic device. The electronic device 101b may further include a connector cover (not shown) to cover at least part of, e.g., the connector hole 109a so that undesirable materials (e.g. dirt) are prevented from entering the connector hole.

The coupling members 150a and 160a may detachably be fastened to at least portions of the housing 110a via locking members 151a and 161a. The locking members 151a and 161a may include components or parts for coupling, such as pogo pins, and, according to an embodiment, may be replaced with protrusions or recesses formed on/in the coupling members 150a and 160a. For example, the coupling members 150a and 160a may be coupled in such a manner as to be fitted into or over the recesses or protrusions formed on the housing 110. The coupling members 150a and 160a may include one or more of a fastening member 152a, fastening member coupling holes 153a, a band guide member 154a, and a band fastening ring 155a.

The fastening member 152a may be configured to allow the housing 110a and the coupling members 150a and 160a to be fastened to the user's body (e.g., wrist or ankle). The fastening member coupling holes 153a may fasten the housing 110a and the coupling members 150a and 160a to the user's body, corresponding to the fastening member 152a. The band guide member 154a may be configured to restrict movement of the fastening member 152a to a certain range when the fastening member 152a fits into one of the fastening member coupling holes 153a, thereby allowing the coupling members 150a and 160a to be tightly fastened onto the user's body. The band fastening ring 155a may limit the range of movement of the coupling members 150a and 160a, with the fastening member 152a fitted into one of the fastening member coupling holes 153a.

Figure 1D:
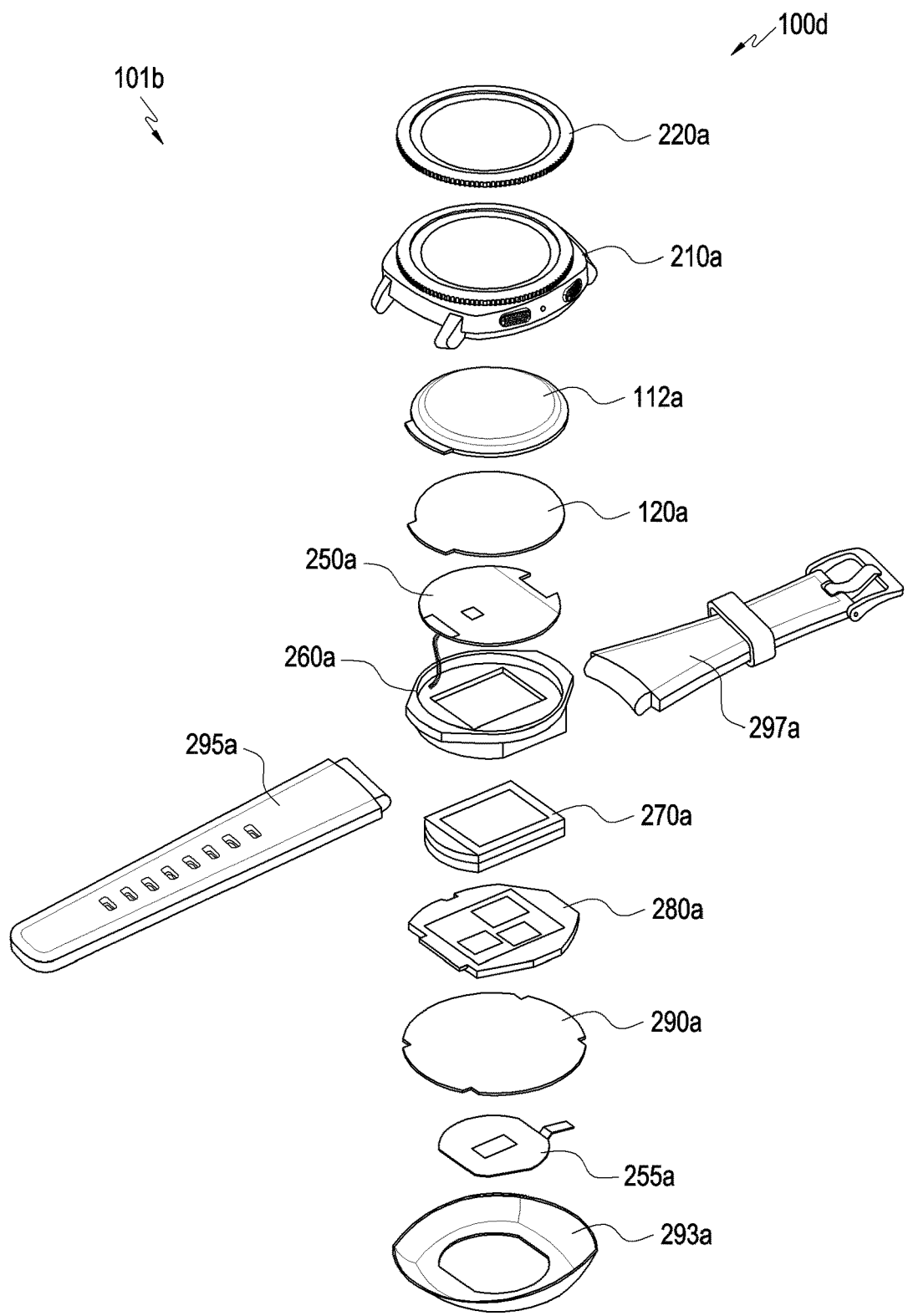
FIG. 1D is an exploded perspective view illustrating an electronic device as shown in FIG. 1B.

FIG. 1D is an exploded perspective view 100d illustrating the electronic device 101b of FIG. 1B.

Referring to FIG. 1D, an electronic device 101b (e.g., the electronic device 101 of FIG. 1A) may include a side bezel structure 210a, a wheel key 220a, a front plate 112a, a display 120a, a first antenna 250a, a second circuit board 255a, a supporting member 260a (e.g., a bracket), a battery 270a, a printed circuit board 280a, a sealing member 290a, a rear plate 293a, and coupling members 295a and 297a. At least one of the components of the electronic device 101b may be the same or similar to at least one of the components of the electronic device 101b of FIG. 1A or 1C and no duplicate description is made below. The supporting member 260a may be disposed inside the electronic device 101b to be connected with the side bezel structure 210a or integrated with the side bezel structure 210a. The supporting member 260a may be made of metal and/or non-metallic material (e.g., polymer). The display 120a may be joined onto one surface of the supporting member 260a, and the printed circuit board 280a may be joined onto the opposite surface of the supporting member 260a. Processor, memory, and/or interface may be mounted on the printed circuit board 280a. The processor may include one or more of, e.g., a central processing unit, an application processor, a graphic processing unit (GPU), a sensor processor, or a communication processor. The processor may include a microprocessor or any suitable type of processing circuitry, such as one or more general-purpose processors (e.g., ARM-based processors), a Digital Signal Processor (DSP), a Programmable Logic Device (PLD), an Application-Specific Integrated Circuit (ASIC), a Field-Programmable Gate Array (FPGA), a Graphical Processing Unit (GPU), a video card controller, etc. In addition, it would be recognized that when a general purpose computer accesses code for implementing the processing shown herein, the execution of the code transforms the general purpose computer into a special purpose computer for executing the processing shown herein. Certain of the functions and steps provided in the Figures may be implemented in hardware, software or a combination of both and may be performed in whole or in part within the programmed instructions of a computer. No claim element herein is to be construed under the provisions of 35 U.S.C. § 112(f), unless the element is expressly recited using the phrase "means for." In addition, an artisan understands and appreciates that a "processor" or "microprocessor" may be hardware in the claimed disclosure. Under the broadest reasonable interpretation, the appended claims are statutory subject matter in compliance with 35 U.S.C. § 101.

The memory may include, e.g., a volatile or non-volatile memory. The interface may include, e.g., a high definition multimedia interface (HDMI), a universal serial bus (USB) interface, a secure digital (SD) card interface, and/or an audio interface. The interface may electrically or physically connect the electronic device 101b with an external electronic device and may include a USB connector, an SD card/multimedia card (MMC) connector, or an audio connector.

The battery 270a may be a device for supplying power to at least one component of the electronic device 101b. The battery 270a may include, e.g., a primary cell which is not rechargeable, a secondary cell which is rechargeable, or a fuel cell. At least a portion of the battery 270a may be disposed on substantially the same plane as the printed circuit board 280a. The battery 270a may be integrally or detachably disposed inside the electronic device 101b.

The first antenna 250a may be disposed between the display 120a and the supporting member 260a. The first antenna 250a may include, e.g., a near-field communication (NFC) antenna, a wireless charging antenna, and/or a magnetic secure transmission (MST) antenna. The first antenna 250a may perform short-range communication with an external device, wirelessly transmit/receive power necessary for charging the electronic device 101b, or transmit magnetic-based signals including payment data or short-range communication signals. According to an embodiment, the antenna structure for the first antenna 250a may be formed by a portion or combination of the side bezel structure 210a and/or the supporting member 260a.

The second circuit board 255a may be disposed between the circuit board 280a and the rear plate 293a. The second circuit board 255a may include an antenna, e.g., a near-field communication (NFC) antenna, a wireless charging antenna, and/or a magnetic secure transmission (MST) antenna. The second circuit board 255a may perform short-range communication with an external device, wirelessly transmit/receive power necessary for charging the electronic device 101b, or transmit magnetic-based signals including payment data or short-range communication signals. According to an embodiment, an antenna structure for the antenna of the second circuit board 255a may be formed by a portion or combination of the side bezel structure 210a and/or the rear plate 293a. According to an embodiment, when the electronic device 101b (e.g., the electronic device 101b of FIG. 1B or 1C) includes a sensor module (e.g., the sensor module 165 of FIG. 1B), a sensor element (e.g., a photoelectric conversion element or electrode pad) separate from the second circuit board 255a or the sensor circuit disposed on the second circuit board 255a may be disposed in the electronic device 101b. For example, an electronic component referred to as the sensor module 165 may be disposed between the circuit board 280a and the rear plate 293a.

The sealing member 290a may be positioned between the side bezel structure 210a and the rear plate 293a. The sealing member 290a may be configured to block moisture or foreign materials from entering the space surrounded by the side bezel structure 210a and the rear plate 293a.

Figure 2:
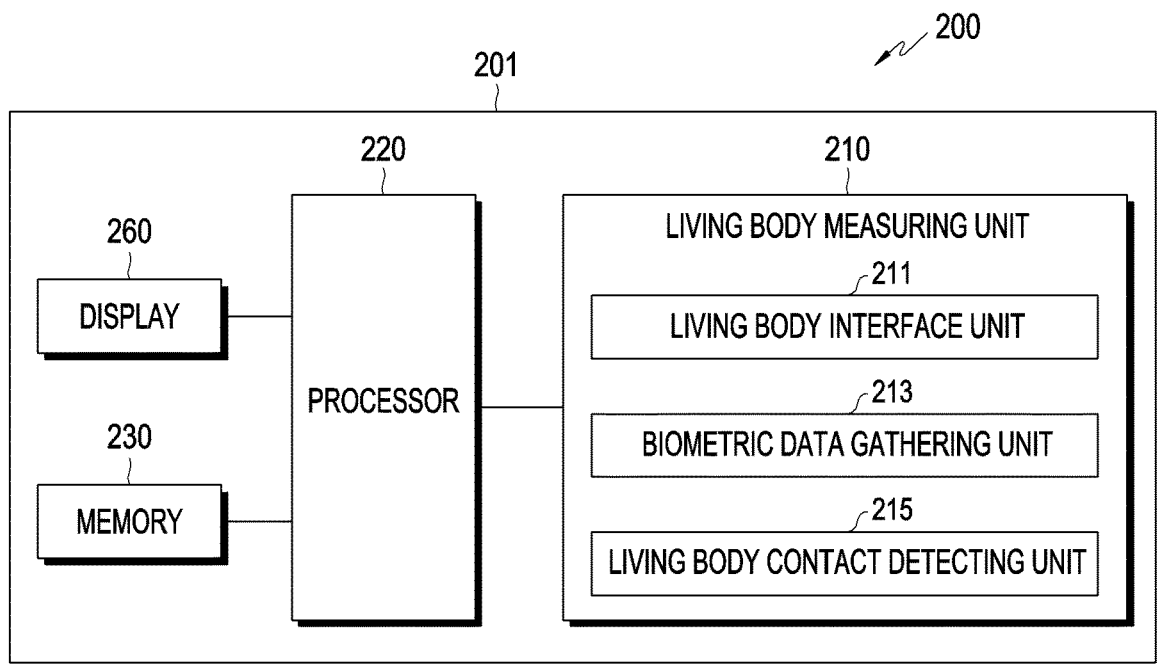
FIG. 2 is a block diagram schematically illustrating a wearable electronic device according to an embodiment.

FIG. 2 is a block diagram 200 schematically illustrating a wearable electronic device according to an embodiment.

Referring to FIG. 2, the wearable electronic device 201 (e.g., the electronic devices 101a to 101d of FIGS. 1A to 1D) may include a living body measuring unit 210, a processor 220, a memory 230, and a display 260.

According to an embodiment, the living body measuring unit 210 may detect contact of a portion of a living body to the electronic device and measure a biometric signal. The living body measuring unit 210 may include a living body interface unit 211, a biometric data gathering unit 213, and a living body contact detecting unit 215.

According to an embodiment, the living body interface unit 211 may include at least one electrode directly contacting the living body. The living body interface unit 211 may electrically contact the living body to be able to exchange electrical signals between the living body and the biometric data gathering unit 213 or the living body contact detecting unit 215.

According to an embodiment, the biometric data gathering unit 213 may detect an electrical signal received via the at least one electrode, thereby generating a biometric signal.

The biometric signal may be transferred to the processor 220 for analysis of the biometric signal via an analog-to-digital converter (ADC).

According to an embodiment, the living body contact detecting unit 215 may determine the operation state for biometric signal measurement of the wearable electronic device 201 using two electrodes included in the living body interface unit 211 and may analyze the biometric signal generated from the biometric data gathering unit 213 to thereby measure the biometric signal.

According to an embodiment, the living body contact detecting unit 215 may apply different voltages to at least two electrodes when they are contacting the living body among for biometric signal measurement. The living body contact detecting unit 215 may output information indicating the operation state of the biometric signal measurement of the wearable electronic device 201 based on the voltage output from the at least two electrodes.

According to an embodiment, the living body contact detecting unit 215 may apply a first voltage to a first electrode when the first electrode among the at least two electrodes for biometric signal measurement contacts a first portion (e.g., wrist) of the living body. The living body contact detecting unit 215 may output information indicating that the operation state of the wearable electronic device 201 is a state of preparing for biometric signal measurement (this state may be referred to as a biometric signal measurement-ready state) based on the first voltage applied to the first electrode. When the first electrode and the third electrode, among the at least two electrodes contact a first portion (e.g., wrist) of the living body and a second portion (e.g., finger) of the living body contact, respectively, the living body contact detecting unit 215 may apply a second voltage different from the first voltage to each of the first electrode and the third electrode. The living body contact detecting unit 215 may output information indicating that the operation state of the wearable electronic device 201 is in a state where the biometric signal may be measured (this state may be referred to as a 'biometric signal measurement-capable state'), based on the first voltage and the second voltage applied to the first electrode and the third electrode, respectively.

According to an embodiment, when the first electrode for measuring the biometric signal and the second electrode for applying a voltage contact the first portion (e.g., wrist) of the living body, the living body contact detecting unit 215 may form a path between the first electrode and the second electrode, thereby generating a closed loop between the first electrode and the second electrode via the first portion (e.g., wrist) of the living body. As the path is formed between the first electrode and the second electrode, the living body contact detecting unit 215 may output first information indicating that the operation state of the wearable electronic device 201 is the biometric signal measurement-ready state, based on the first voltage applied from the second electrode to the first electrode. When the third electrode for measuring the biometric signal contacts the second portion (e.g., finger) of the living body while the first information is output, the living body contact detecting unit 215 may form an additional path between the second electrode and the third electrode. The living body contact detecting unit 215 may output second information indicating that the operation state of the wearable electronic device 201 is the biometric signal measurement-capable state, based on the second voltage (different from the first voltage), which is applied from the second electrode to each of the first electrode and the third electrode.

According to an embodiment, when the first electrode and the third electrode contact no portion of the living body while the second information is output, the living body contact detecting unit 215 may output, from the second electrode, third information indicating that the operation state of the wearable electronic device is a state in which the biometric signal measurement has stopped (this state is referred to as a biometric signal measurement-stopped state), based on a voltage (e.g., 0V) output from the third electrode and the first electrode to which no voltage is applied.

According to an embodiment, the living body contact detecting unit 215 may measure the biometric signal using the difference between the potential values measured at the at least two electrodes for biometric signal measurement.

The living body contact detecting unit 215 is described below with reference to FIG. 3.

According to an embodiment, the processor 220 (e.g., the processor 120 of FIG. 1A) may control the overall operation of the wearable electronic device 201.

According to an embodiment, the processor 220 (e.g., the processor 120 of FIG. 1A) may determine the operation state for biometric signal measurement of the wearable electronic device 201 based on information output from the living body contact detecting unit 215.

According to an embodiment, upon receiving first information indicating that the operation state of the wearable electronic device 201 is the biometric signal measurement-ready state, the processor 220 may switch to the biometric signal measurement (e.g., ECG measurement)-ready state. For example, the processor 220 may detect an application capable of biometric signal measurement and prepare for executing the same. In the biometric signal measurement-ready state, the processor 220 may measure the heartrate based on the signal received via the photoplethysmography (PPG) sensor (415 of FIG. 4A) mounted on the rear surface of the wearable electronic device 201.

According to an embodiment, upon receiving second information indicating that the operation state of the wearable electronic device 201 is the biometric signal measurement-capable state, the processor 220 may switch to the biometric signal measurement-capable state (e.g., the state where of ECG is measured).

According to an embodiment, upon receiving third information indicating that the operation state of the wearable electronic device 201 is the biometric signal measurement-stopped state in the biometric signal measurement-capable state, the processor 220 may switch to the biometric signal measurement-stopped state. In this state, measurement of biometric signal may be stopped.

According to an embodiment, upon receiving first information indicating that the operation state of the wearable electronic device 201 is the biometric signal measurement-ready state, the processor 220 may switch to the biometric signal measurement-ready state and then maintain the session for the biometric signal measurement-ready state. Upon receiving second information indicating that the operation state of the wearable electronic device 201 is the biometric signal measurement-capable state while maintaining the session for the biometric signal measurement-ready state, the processor 220 may automatically switch to the biometric signal measurement-capable state and measure the biometric signal.

According to an embodiment, upon receiving first information indicating that the operation state of the wearable electronic device 201 is the biometric signal measurement-ready state, the processor 220 may display that the wearable electronic device 201 is currently in the biometric signal measurement-ready state, via a user interface (UI), on the display 260. Upon receiving second information indicating that the operation state of the wearable electronic device 201 is the biometric signal measurement-capable state while displaying that the wearable electronic device 201 is currently in the biometric signal measurement-ready state, the wearable electronic device 201 may display, via the UI on the display 260, that the wearable electronic device 201 is in the state of currently measuring the biometric signal.

According to an embodiment, the memory 230 may store data (e.g., biometric signal data) from the wearable electronic device 201. The memory 230 may be implemented in substantially the same or similar manner to the memory 130 described above in connection with FIG. 1A. The memory 230 may be implemented as a non-volatile memory.

According to an embodiment, the display 260 may be implemented in substantially the same or similar manner to the display device 160 described above in connection with FIG. 1A. The display 260 may display, via the UI, information indicating that the wearable electronic device is operating in the biometric signal measurement-ready state or information indicating that the wearable electronic device is operating in the state of measuring the biometric signal. When the electrodes of the wearable electronic device do not contact any portion of the living body in the state of measuring the biometric signal, the display 260 may display, via the UI, information indicating the biometric signal measurement-stopped state.

Figure 3:
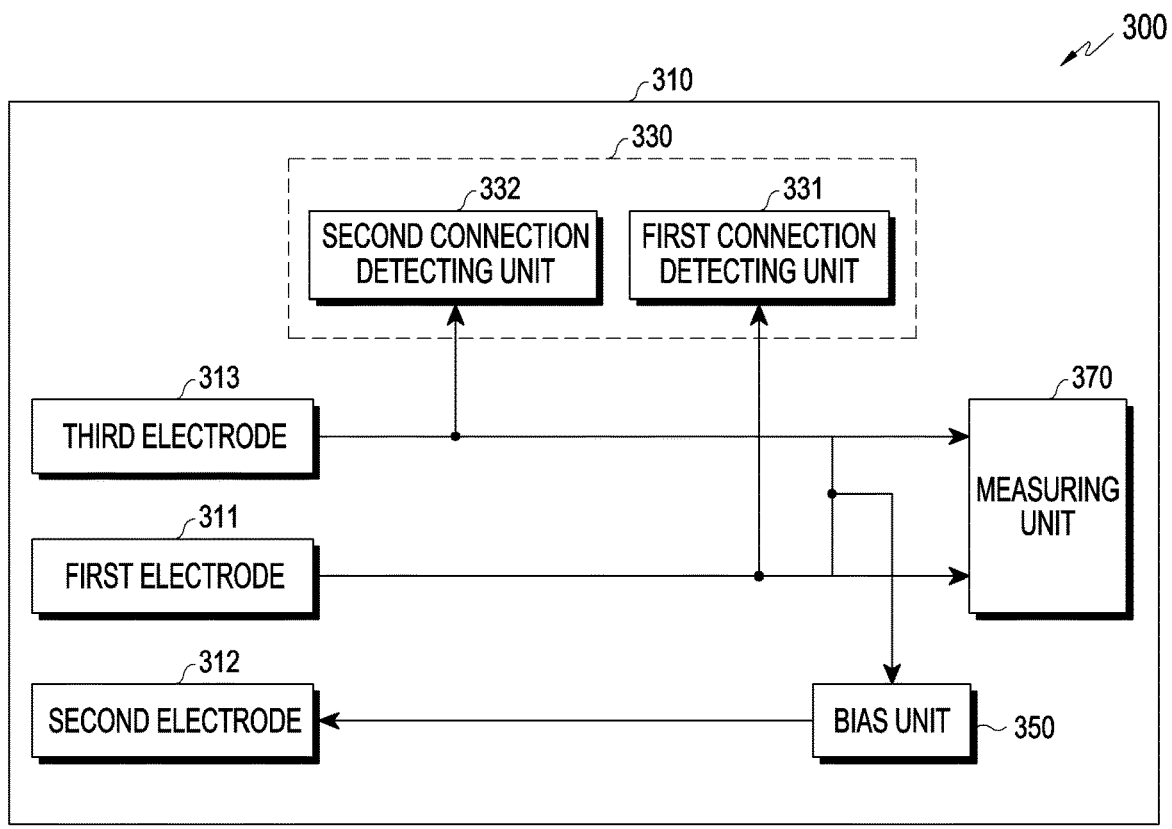
FIG. 3 is a block diagram schematically illustrating a living body contact detecting unit of a wearable electronic device according to an embodiment.

FIG. 3 is a block diagram 300 schematically illustrating a living body contact detecting unit of a wearable electronic device according to an embodiment.

Referring to FIG. 3, a living body contact detecting unit 310 (e.g., the living body contact detecting unit 215 of FIG. 2) may include a plurality of electrodes 311, 312, and 313, an electrode connection detecting unit 330, a bias unit 350, and a measuring unit 370.

According to an embodiment, the plurality of electrodes may include a first electrode 311 and a third electrode 313 for measuring a biometric signal and a second electrode 312 for applying a voltage to the first electrode 311 and/or the third electrode 313.

According to an embodiment, the first electrode 311 and the third electrode 313 may include sensing electrodes capable of measuring a biometric signal at both ends (e.g., right hand and/or left hand) of the living body.

According to an embodiment, the first electrode 311 may be mounted in a position where a first portion (e.g., wrist) of the living body may come into contact with it, and the third electrode 313 may be mounted in a position where a second portion (e.g., finger) of the living body may come into contact with it. The third electrode 313 may be mounted in a position different from the positions where the first electrode 311 and the second electrode 312 are mounted, and the second portion (e.g., finger) of the living body may contact the third electrode 313.

According to an embodiment, the second electrode 312 may be positioned on the same surface as the first electrode 311 or the third electrode 313. For example, the second electrode 312 may be positioned on the same surface as the first electrode 311 and may contact the first portion (e.g., wrist) of the living body simultaneously with the first electrode 311.

According to an embodiment, when the second electrode 312 contacts the first portion (e.g., wrist) of the living body simultaneously with the first electrode 311, a path may be formed between the second electrode 312 and the first electrode 311, thereby generating a closed loop between the second electrode 312 and the first electrode 311 via the first portion (e.g., wrist) of the living body, and a first voltage may be applied to the first electrode 311 via the path.

According to an embodiment, when the third electrode 313 contacts the second portion (e.g., finger) of the living body while the first voltage is applied to the first electrode 311 so that an additional path is formed between the second electrode 312 and the third electrode 313, the second electrode 312 may apply the same second voltage to each of the first electrode 311 and the third electrode 313. The second voltage may be lower than the first voltage.

According to an embodiment, the electrode connection detecting unit 330 may output information indicating the operation state for biometric signal measurement of the wearable electronic device (e.g., the wearable electronic device 201 of FIG. 2), based on the voltage output from the first electrode 311 and/or the third electrode 313.

According to an embodiment, the electrode connection detecting unit 330 may output first information indicating that the operation state of the wearable electronic device is the biometric signal measurement-ready state, based on the voltage (e.g., the first voltage or the second voltage) output from the first electrode 311.

According to an embodiment, the electrode connection detecting unit 330 may output second information indicating that the operation state of the wearable electronic device is the biometric signal measurement-capable state, based on the second voltage output from the first electrode 311 and the third electrode 313.

According to an embodiment, when the first electrode 311 and the third electrode 313 contact no portion of the living body, the electrode connection detecting unit 330 may output, from the second electrode 312, third information indicating that the operation state of the wearable electronic device is the biometric signal measurement-stopped state, based on no voltage (e.g., 0V) output from the third electrode 313 and the first electrode 311.

According to an embodiment, the electrode connection detecting unit 330 may include a first connection detecting unit 331, which outputs a first comparison value resultant from comparing a first reference voltage with the first voltage and/or second voltage output from the first electrode 311. The electrode connection detecting unit 330 may further include a second connection detecting unit 332, which outputs a second comparison value resultant from comparing a second reference voltage with the second voltage output from the third electrode 313. The electrode connection detecting unit 330 may summate the first comparison value output from the first connection detecting unit 331 and the second comparison value output from the second connection detecting unit 332 and output the summated value as information indicating the operation state for biometric signal measurement of the wearable electronic device.

According to an embodiment, the bias unit 350 may adjust the voltage to be applied to the first electrode 311 and/or third electrode 313, when the paths are formed with the second electrode 312, to the first voltage and/or the second voltage.

According to an embodiment, the bias unit 350 may be configured as an inverting summing amplifier.

According to an embodiment, the measuring unit 370 may measure the biometric signal using the difference between the potential values measured at the first electrode 311 and the third electrode 313.

According to an embodiment, the measuring unit 370 may include a differential amplifier or an instrumentation amplifier (IA) having very high input impedance.

FIGS. 4A, 4B, 4C, and 4D are views 400a to 400d illustrating electrodes of a wearable electronic device according to an embodiment.

Figure 4A:
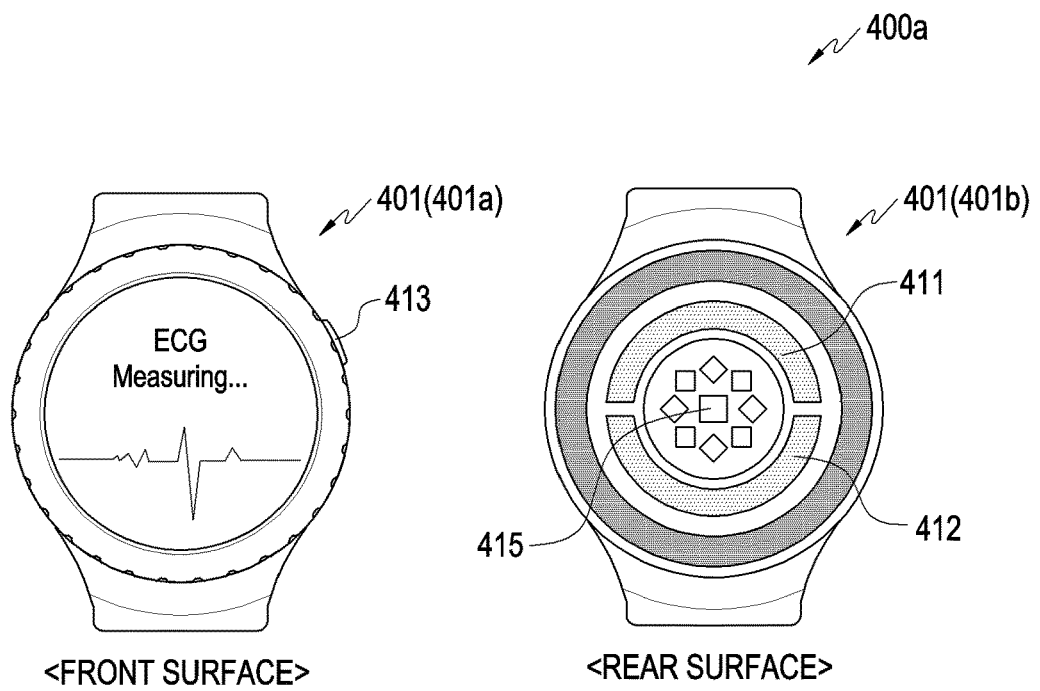
FIGS. 4A, 4B, 4C, and 4D are views illustrating electrodes of a wearable electronic device according to an embodiment.

FIG. 4A illustrates a front surface 401a and rear surface 401b of a wearable electronic device 401.

Referring to FIG. 4A, a first electrode 411 (e.g., the first electrode 311 of FIG. 3) for measuring biometric signals may be disposed on the rear surface 401b of the wearable electronic device 401, and a second electrode 412 (e.g., the second electrode 312 of FIG. 3) for applying voltage to the first electrode 411 and a third electrode 413 (e.g., the third electrode 313 of FIG. 3) may be disposed on the same surface as the first electrode 411. The third electrode 413 for measuring biometric signals may be disposed on a side surface of the wearable electronic device 401 which may be contacted by the other hand of the user when the wearable electronic device 401 is worn on one hand. A photoplethysmography (PPG) sensor 415 for heartrate measurement may be mounted in the center on the rear surface 401b of the wearable electronic device 401.

Figure 4B:
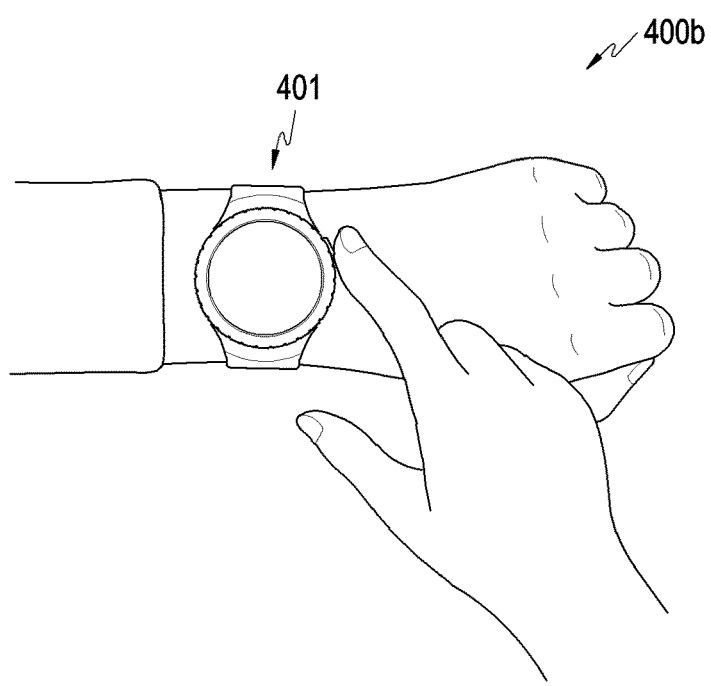

As shown in FIG. 4B, the wearable electronic device 401 may be worn on the user's wrist, and a first portion (e.g., the user's wrist) of the user's body may come in contact with the first electrode 411 and the second electrode 412, and a second portion (e.g., the user's finger) of the user's body may come in contact with the third electrode 413 placed on the right side surface of the wearable electronic device 401.

The third electrode which may be touched by the second portion (e.g., finger) of the user's body, with the wearable electronic device 401 worn on the user's wrist and the first portion (e.g., wrist) of the user's body contacting the first electrode 411 and the second electrode 412, may be disposed in various positions. For example, the third electrode 413 may be disposed on the left side surface of the wearable electronic device 401 or, as shown in FIG. 4B, on the right side surface.

Figure 4C:
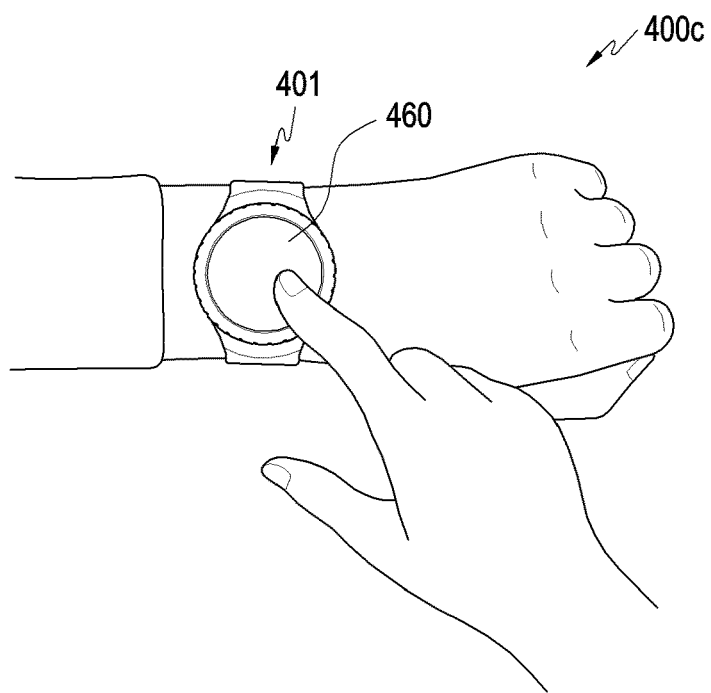

Alternatively, as shown in FIG. 4C, the third electrode 413 may be included, as a transparent electrode, in the display 460 (e.g., the display 120a of FIG. 1D or the display 260 of FIG. 2) of the wearable electronic device 401 and be contacted by a second portion (e.g., finger) of the user's body.

Figure 4D:
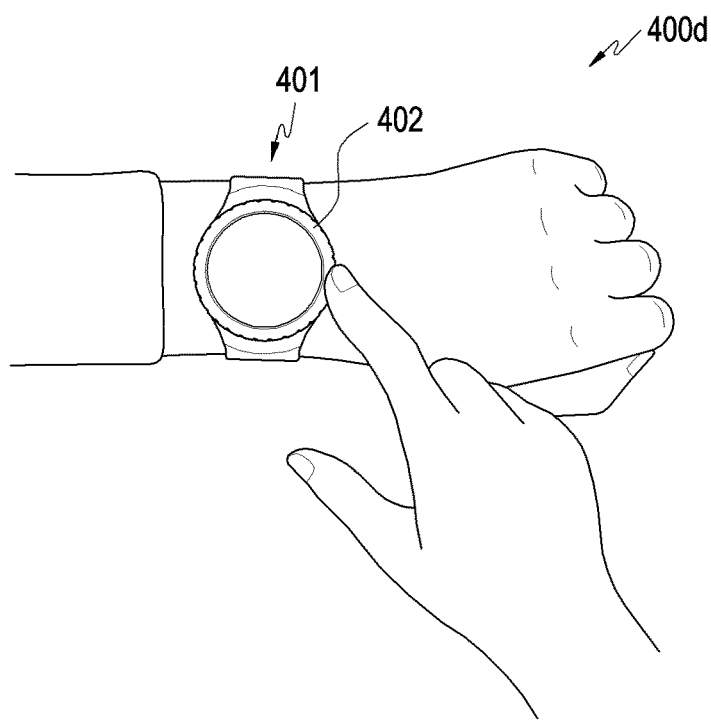

Alternatively, as shown in FIG. 4D, the third electrode 413 may be disposed in the bezel 402 (e.g., 106a of FIG. 1B) of the wearable electronic device 401 and be contacted by the second portion (e.g., finger) of the user's body. When the wearable electronic device 401 is bezel-less, the third electrode 413 may be disposed on the housing (e.g., 110a of FIG. 1B) of the wearable electronic device 401 and be contacted by the second portion (e.g., finger) of the user's body.

Figure 5:
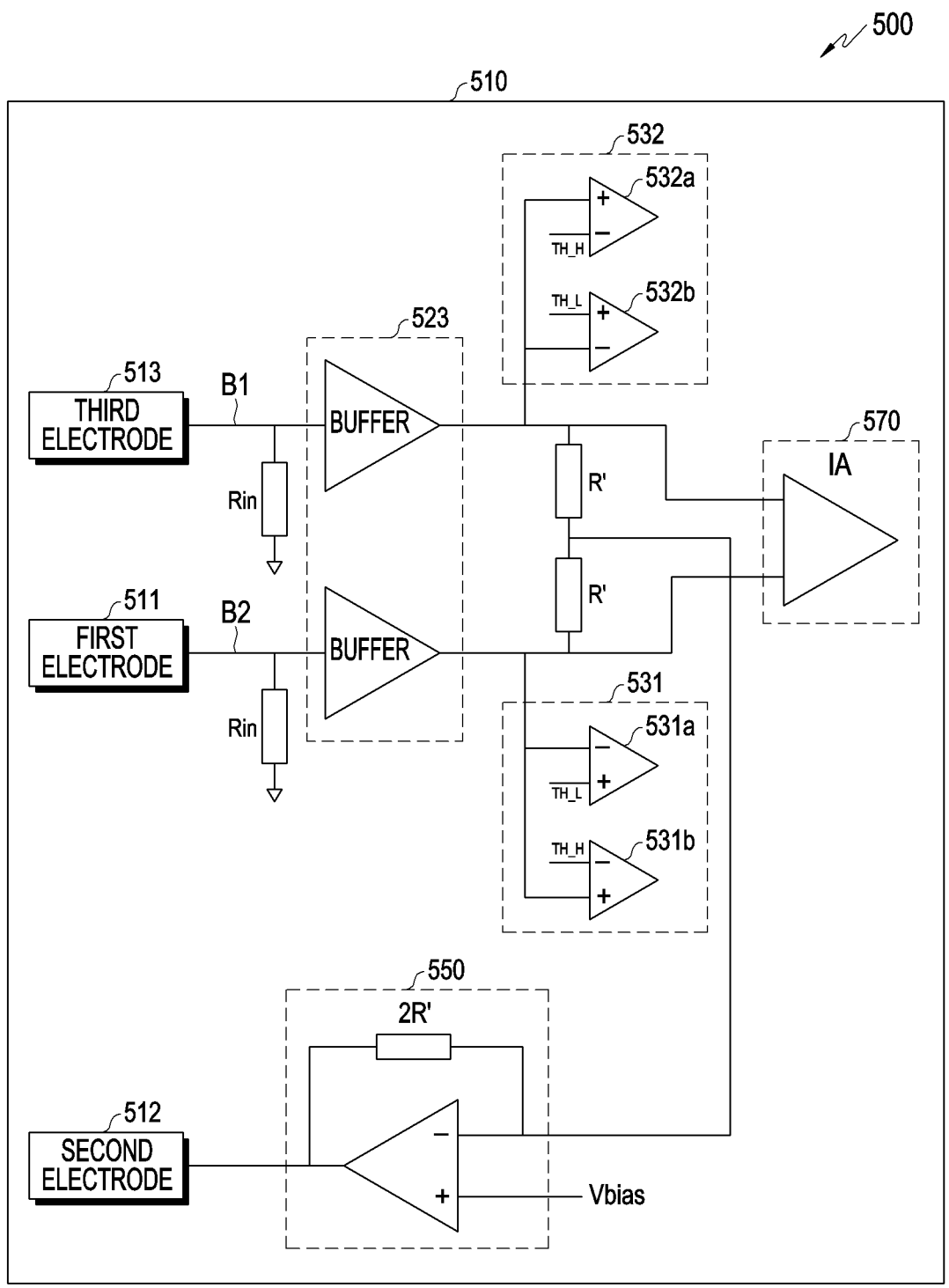
FIG. 5 is a circuit diagram illustrating a living body contact detecting unit of a wearable electronic device according to an embodiment.

FIG. 5 is a circuit diagram 500 illustrating a living body contact detecting unit of a wearable electronic device according to an embodiment. FIG. 5 is a circuit diagram of the living body contact detecting unit 310 of the wearable electronic device of FIG. 3.

Referring to FIG. 5, the living body contact detecting unit 510 may include a plurality of electrodes 511, 512, and 513, a plurality of buffers 523 having high input impedance, which process the voltage output from the first electrode 511 and third electrode 513 for biometric signal measurement, electrode connection detecting units 531 and 532, a bias unit 550, and a measuring unit 570 measuring the biometric signal based on the first electrode 511 and the third electrode 513.

The plurality of electrodes may include a first electrode 511 and a third electrode 513 for measuring a biometric signal and a second electrode 512 for applying a predetermined voltage to the first electrode 511 and the third electrode 513.

The electrode connection detecting units 531 and 532 may include a first connection detecting unit 531 comparing a first reference voltage with the first voltage and/or second voltage output from the first electrode 511 and a second connection detecting unit 532 comparing a second reference voltage with the second voltage output from the third electrode 513.

The first connection detecting unit 531 may include a first comparator 531a and a second comparator 531b and may set the first reference voltage TH_L of the first comparator 531a to "0.4V" and the first reference voltage TH_H of the second comparator 531b to "1.4V."

According to an embodiment, the first reference voltage TH_L of the first comparator 531a and the first reference voltage TH_H of the second comparator 531b may be adjusted by the processor (e.g., the processor 220 of FIG. 2) for enhancing the detecting capability. The processor may adjust the first reference voltage TH_L of the first comparator 531a and the first reference voltage TH_H of the second comparator 531b according to the operation state for biometric signal measurement of the wearable electronic device. When the operation state for biometric signal measurement of the wearable electronic device is the biometric signal measurement-ready state, the processor may adjust a range of the first reference voltage TH_L of the first comparator 531a and the first reference voltage TH_H of the second comparator 531b to a first range and, when the operation state of biometric signal measurement of the wearable electronic device is the state of measuring the biometric signal, the processor may adjust a range of the first reference voltage TH_L of the first comparator 531a and the first reference voltage TH_H of the second comparator 531b to a second range which is smaller or larger than the first range.

The second connection detecting unit 532 may include a first comparator 532a and a second comparator 532b and may set the second reference voltage TH_H of the first comparator 532a to "1.4V" and the second reference voltage TH_L of the second comparator 532b to "0.4V."

According to an embodiment, the second reference voltage TH_H of the first comparator 532a and the second reference voltage TH_L of the second comparator 532b may be adjusted by the processor (e.g., the processor 220 of FIG. 2) for enhancing the detecting capability. The processor may adjust the second reference voltage TH_H of the first comparator 532a and the second reference voltage TH_L of the second comparator 532b according to the operation state for biometric signal measurement of the wearable electronic device. When the operation state for biometric signal measurement of the wearable electronic device is the biometric signal measurement-ready state, the processor may adjust a range between the second reference voltage TH_H of the first comparator 532a and the second reference voltage TH_L of the second comparator 532b to a third range and, when the operation state of biometric signal measurement of the wearable electronic device is the state of measuring the biometric signal, the processor may adjust a range between the second reference voltage TH_H of the first comparator 532a and the second reference voltage TH_L of the second comparator 532b to a fourth range which is smaller or larger than the third range.

According to an embodiment, the comparator (e.g., the first comparator 531a and second comparator 531b of the first connection detecting unit 531 and/or the first comparator 532a and second comparator 532b of the second connection detecting unit 532) may compare the voltages applied to the non-inverting (+) input terminal and inverting (−) input terminal and output the result of the comparison. For example, when the voltage applied to the non-inverting (+) input terminal is higher than the voltage applied to the inverting (−) input terminal, the comparator may output "1" and, when the voltage applied to the non-inverting (+) input terminal is identical to or lower than the voltage applied to the inverting (−) input terminal, the comparator may output "0." The comparator (e.g., the first comparator 531a and second comparator 531b of the first connection detecting unit 531 and/or the first comparator 532a and second comparator 532b of the second connection detecting unit 532) may compare the voltages applied to the non-inverting (+) input terminal and inverting (−) input terminal based on other various comparison conditions and output the results.

According to an embodiment, the properties of the electrode connection detecting units 531 and 532 may be adjusted according to external factors (e.g., the user's characteristics (e.g., the degree of dryness of hand) and/or ambient environment (e.g., temperature).

According to an embodiment, the properties of the electrode connection detecting units 531 and 532 may be adjusted by increasing the input resistance (Rin) of the front end of the buffer 523 or by changing the operation voltage (e.g., 0.4V) set as default for the comparator (e.g., the first comparator 531a and second comparator 531b of the first connection detecting unit 531 and/or the first comparator 532a and second comparator 532b of the second connection detecting unit 532).

According to an embodiment, the properties of the electrode connection detecting units 531 and 532 may be changed by the user's selection or automatically according to the result of detection by a detecting unit capable of detecting external factors (e.g., the user's characteristics (e.g., the degree of hand dryness) and/or ambient environment (e.g., temperature)).

The electrode connection detecting units 531 and 532 may output the information, which results from summating the information output from the first connection detecting unit 531 and the information output from the second connection detecting unit 532 and list such pieces of information in order, as information (e.g., first information or second information) for indicating the operation state for biometric signal measurement of the wearable electronic device (e.g., the wearable electronic device 201 of FIG. 2).

The bias unit 550 may include an inverting summing amplifier, the average voltage of the first electrode 511 and the third electrode 513 may be input to the inverting (−) terminal of the amplifier, and the Vbias input to the non-inverting (+) terminal may be set to 0.9V. The amplifier may be configured to output 0V through up to 1.8V.

The plurality of buffers 523 are high-impedance elements and may allow high voltage to be applied to the respective front nodes B1 and B2 of the first electrode 511 and the third electrode 513.

Due to their high impedance, the plurality of buffers 523 may stop the current flowing through the front nodes B1 and B2 of the first electrode 511 and the third electrode 513 from flowing towards the plurality of buffers 523, thereby preventing the biometric measurement (e.g., ECG measurement) signal from weakening due to a drop of the voltage applied to the front nodes B1 and B2 of the first electrode 511 and the third electrode 513.

The plurality of buffers 523 may be used for precise biometric measurement (e.g., ECG measurement) signals in the case where the contact resistance increases due to the user's dry skin or a small electrode area as in the wearable electronic device.

The plurality of buffers 523 may not be included in the living body contact detecting unit 510 in the case the electrode impedance is maintained to be lower than a predetermined reference in the wearable electronic device. The plurality of buffers 523 are elements for minimizing influence by the electrode impedance and may be omitted in the system where the electrode impedance is maintained to be lower than a predetermined reference.

Figure 6:
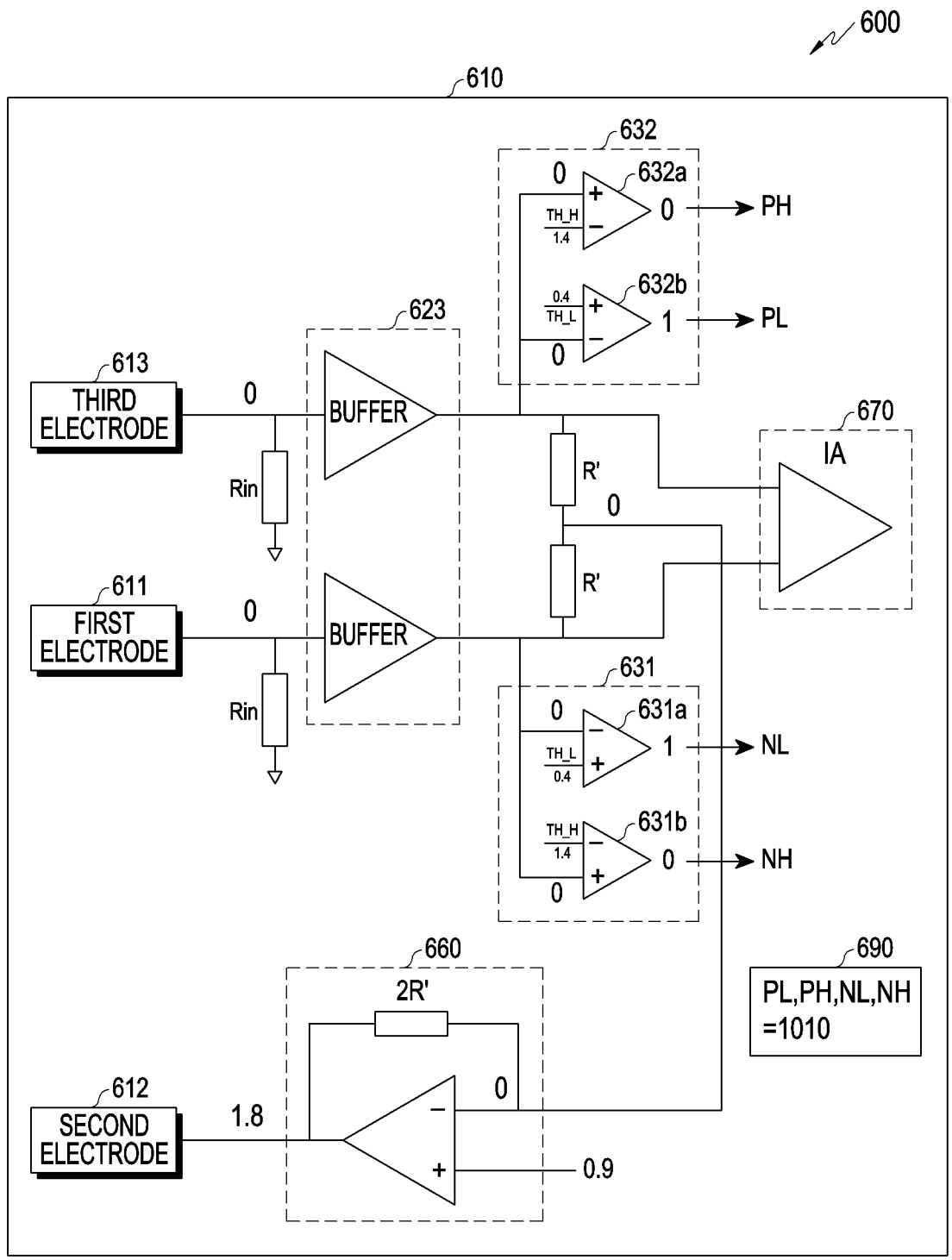
FIG. 6 is a view illustrating an example of detecting living body contact by a wearable electronic device according to an embodiment.

FIG. 6 is a view 600 illustrating an example of detecting living body contact by a wearable electronic device according to an embodiment. FIG. 6 is a view illustrating the biometric signal measurement-stopped state in which no living body contact is made in the wearable electronic device. FIG. 6 illustrates the same living body contact detecting unit 610 as that of FIG. 5, except that different reference numbers are used.

Referring to FIG. 6, with the living body is not in contact with both the first electrode 611 and the third electrode 613 for biometric measurement, the first electrode 611 and the third electrode 613 each may output a voltage of 0V. The first comparator 631a and the second comparator 631b included in the first connection detecting unit 631 may compare the voltage (0V) output from the first electrode 611 with a first reference voltage (TH_L=0.4V, TH_H=1.4V) and output "NL=1, NH=0" as information according to the result of comparison. The first comparator 632a and the second comparator 632b included in the second connection detecting unit 632 may compare the voltage (0V) output from the third electrode 613 with a second reference voltage (TH_H=1.4V, TH_L=0.4V) and output "PL=1, PH=0" as information according to the result of comparison. "PL, PH, NL, NH=1010" (690), which results from summating the information (PL, PH) output from the second connection detecting unit 632 and the information (NL, NH) output from the first connection detecting unit 631 and listing the pieces of information in order, may be output, as third information, to the processor (e.g., the processor 220 of FIG. 2). The processor may detect that the operation state for biometric signal measurement of the wearable electronic device is the biometric signal measurement-stopped state, based on the third information "PL, PH, NL, NH=1010" (690) output from the living body contact detecting unit 610.

FIGS. 7A, 7B, 7C, and 7D are views 700a to 700d illustrating an example of detecting living body contact by a wearable electronic device according to an embodiment. FIGS. 7A to 7D are views illustrating the biometric signal measurement-ready state in the wearable electronic device and show the process from the time when the wearable electronic device contacts the first portion (e.g., wrist) of the living body to the final stable state in which information indicating contact of the first portion (e.g., wrist) of the living body to the wearable electronic device may be output. FIGS. 7A to 7D illustrate the same living body contact detecting unit 710 as that of FIGS. 5 and 6, except that different reference numbers are used.

Figure 7A:
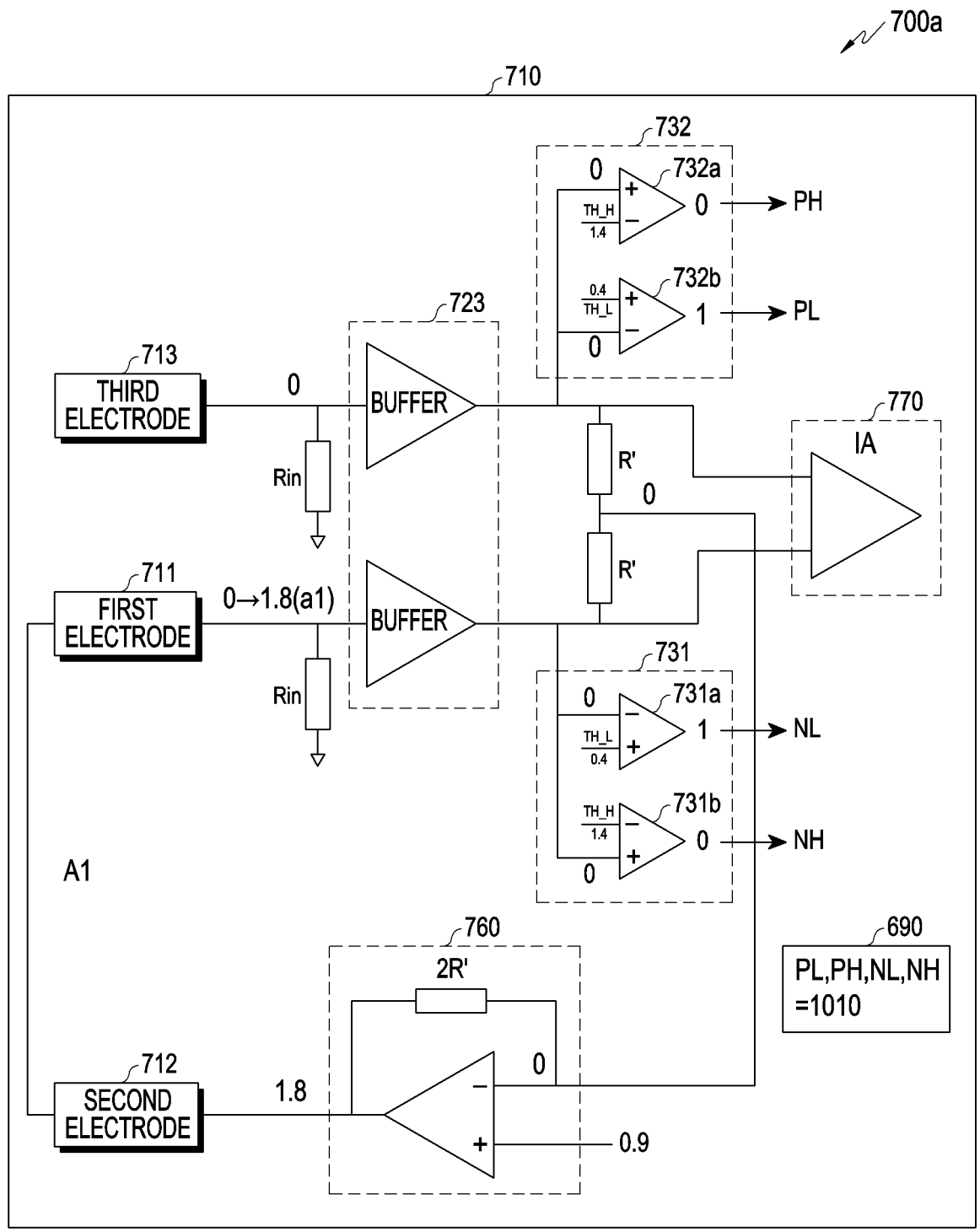
FIGS. 7A, 7B, 7C, and 7D are views illustrating an example of detecting living body contact by a wearable electronic device according to an embodiment.

Referring to FIG. 7A, when the wearable electronic device is worn on the user's wrist, the first electrode 711 and second electrode 712 positioned on the same surface may contact the first portion (e.g., wrist) of the living body. When the first electrode 711 and the second electrode 712 contact the first portion (e.g., wrist) of the living body so that a path A1 is formed between the first electrode 711 and the second electrode 712, the second electrode 712 may apply a first voltage, e.g., maximum voltage Vsat of 1.8V, to the first electrode 711 (a1).

Figure 7B:
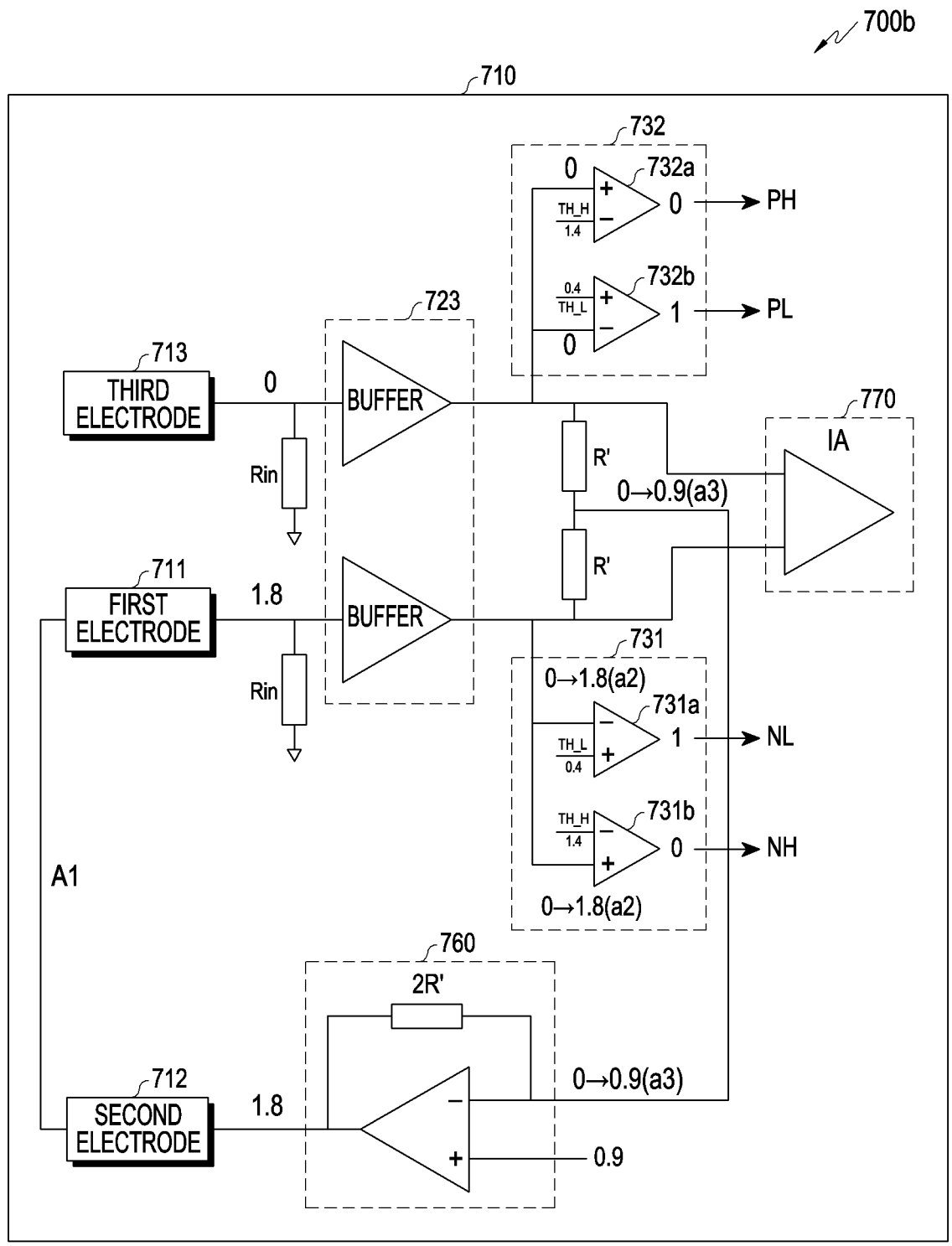

Referring to FIG. 7B, when the maximum voltage, 1.8V, is applied from the second electrode 712 to the first electrode 711, a voltage of 1.8V output from the first electrode 711 may be input to each of the first comparator 731a and the second comparator 731b included in the first connection detecting unit 731 (a2). As the third electrode 713 which the living body does not contact outputs 0V, the first comparator 732a and the second comparator 732b included in the second connection detecting unit 732 may maintain input of 0V which is output from the third electrode 713. The average voltage, 0.9V, of the first electrode 711 and the third electrode 713 may be input to the inverting (−) terminal of the bias unit 760 (a3).

Figure 7C:
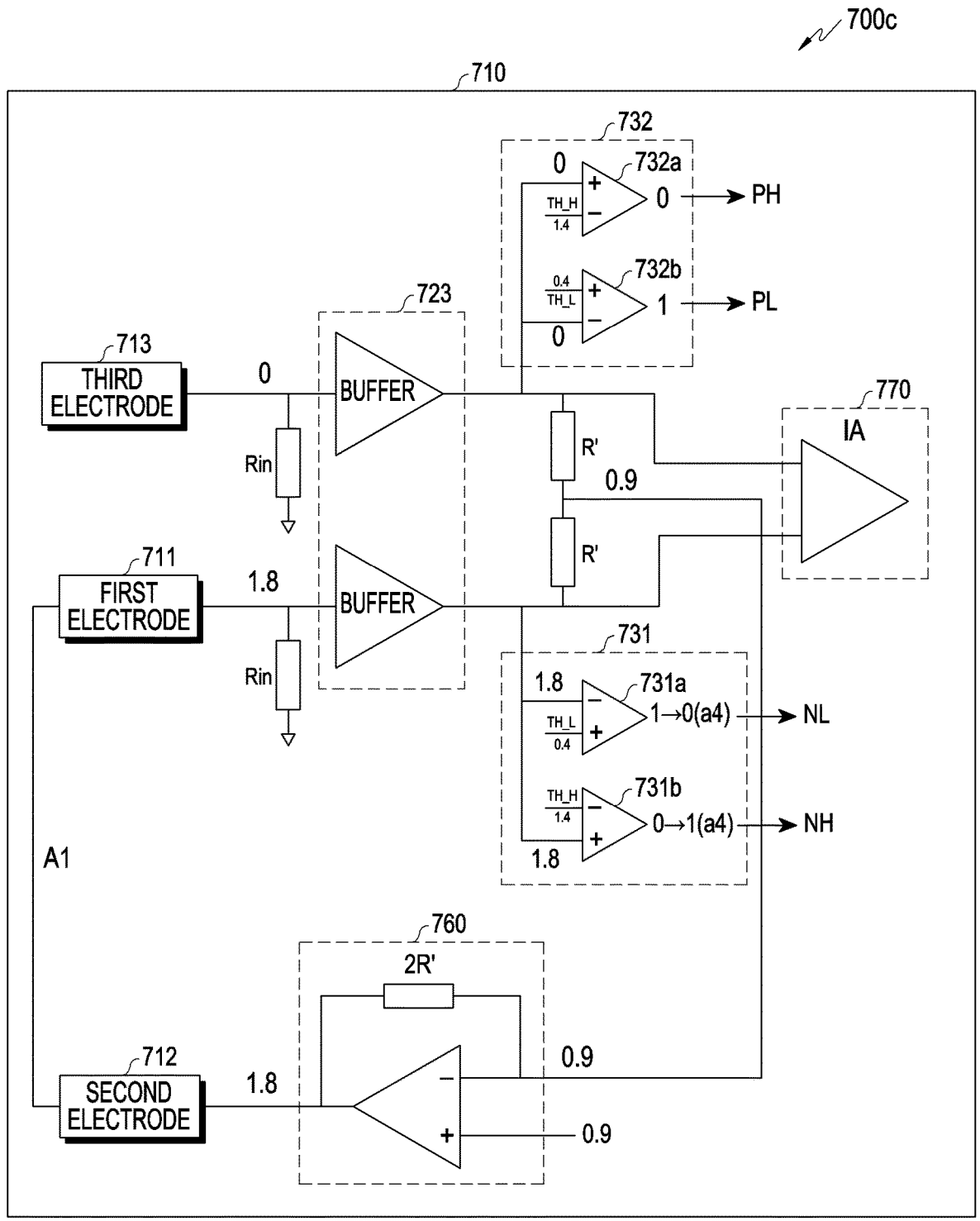

Referring to FIG. 7C, 1.8V which is input to each of the first comparator 731a and the second comparator 731b included in the first connection detecting unit 731 may be compared with the first reference voltage (TH_L=0.4V, TH_H=1.4V), and "NL=0, NH=1," as information according to the result of comparison, may be output (a4). The first comparator 732a and the second comparator 732b included in the second connection detecting unit 732 may compare the voltage (0V) output from the third electrode 713 with a second reference voltage (TH_H=1.4V, TH_L=0.4V) and maintain the output of "PL=1, PH=0" as information according to the result of comparison.

Figure 7D:
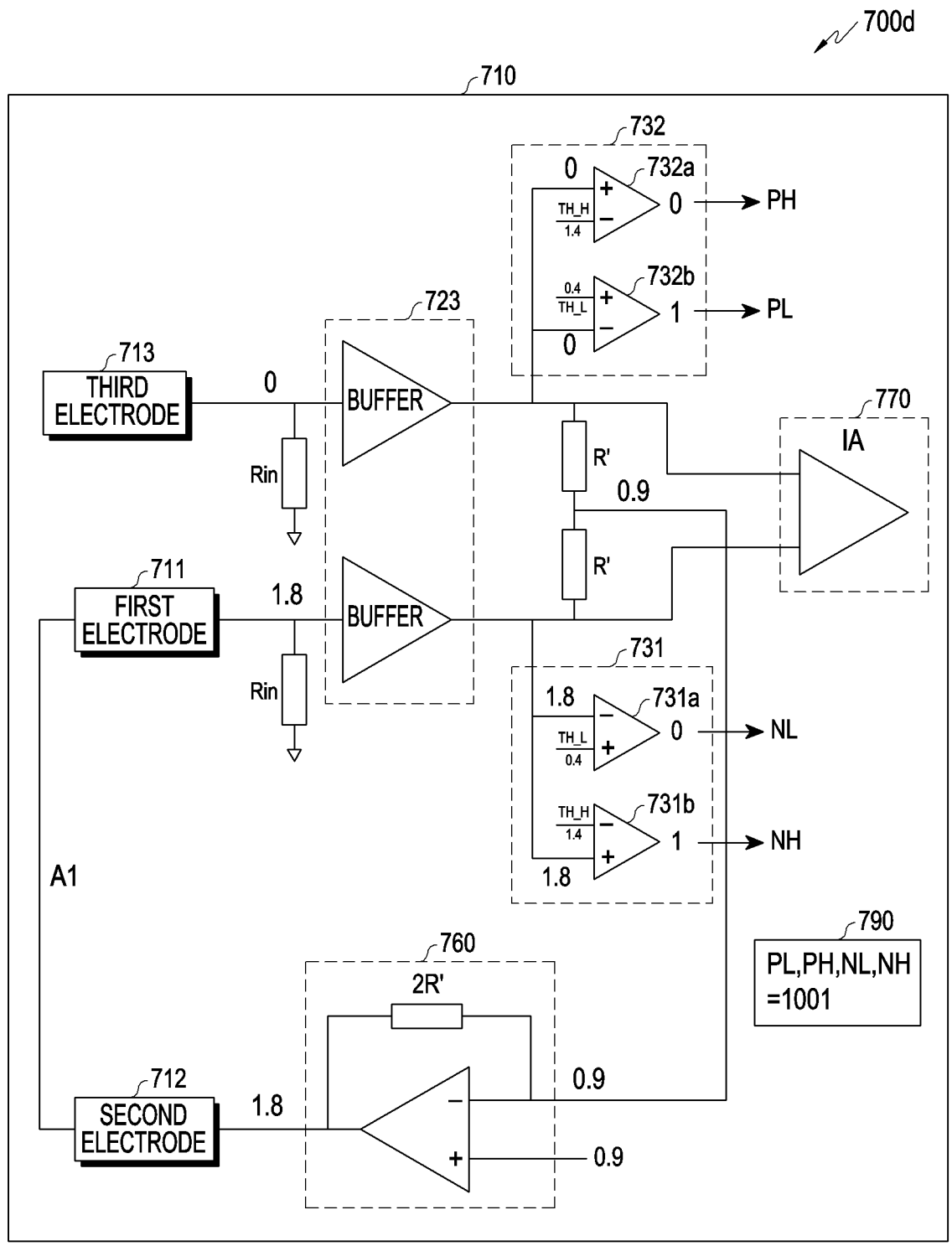

By the process shown in FIGS. 7A to 7C, when the final stable state is reached as shown in FIG. 7D, "PL, PH, NL, NH=1001" (790), which results from summating the information (PL, PH) output from the second connection detecting unit 732 and the information (NL, NH) output from the first connection detecting unit 731 and listing the pieces of information in order, may be output, as first information, to the processor (e.g., the processor 220 of FIG. 2). The processor may detect that the operation state for biometric signal measurement of the wearable electronic device is the biometric signal measurement-ready state, based on the first information "PL, PH, NL, NH=1001" (790) output from the living body contact detecting unit 710.

Figure 8A:
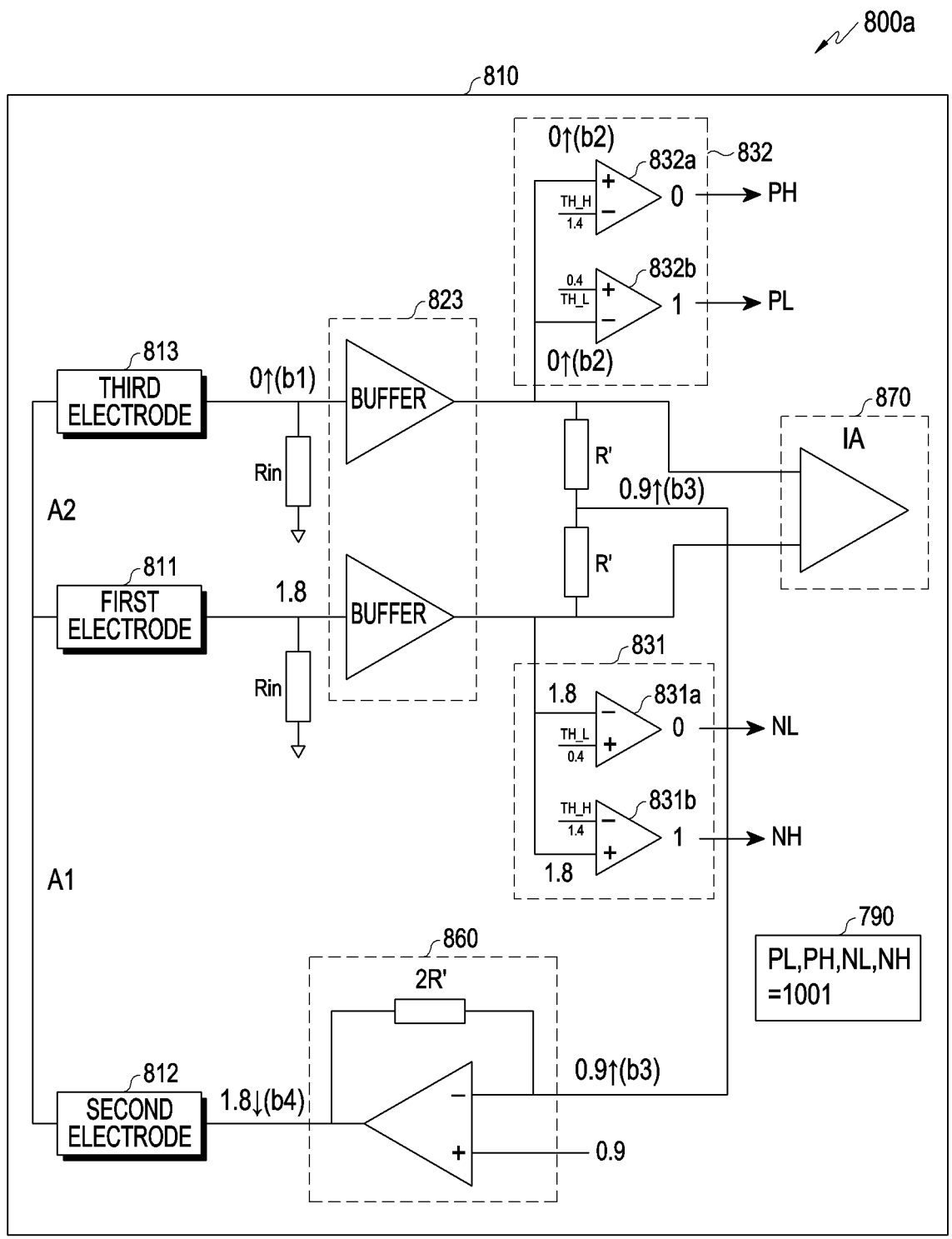
FIGS. 8A, 8B, and 8C are views illustrating an example of detecting living body contact by a wearable electronic device according to an embodiment.
Figure 8B:
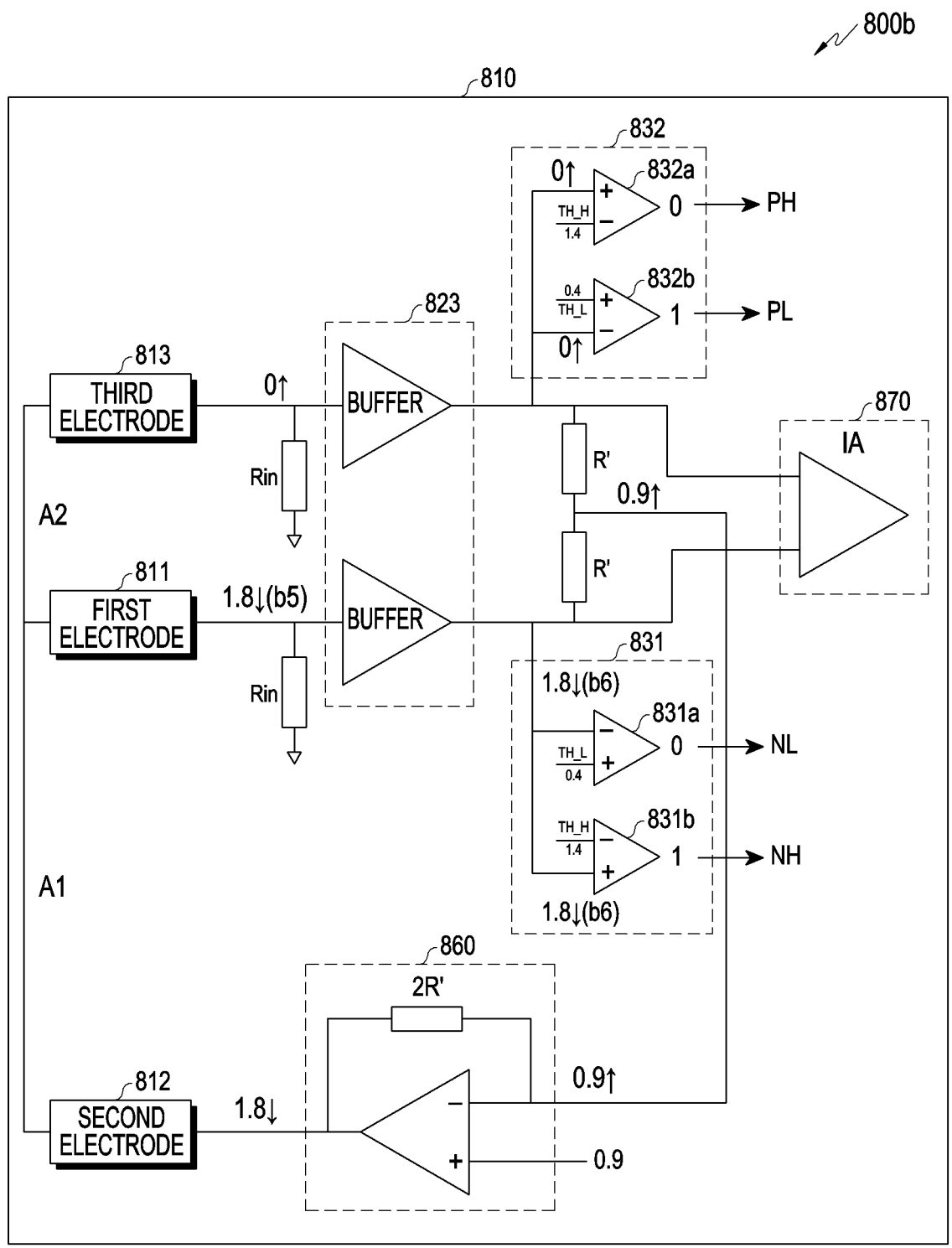
Figure 8C:
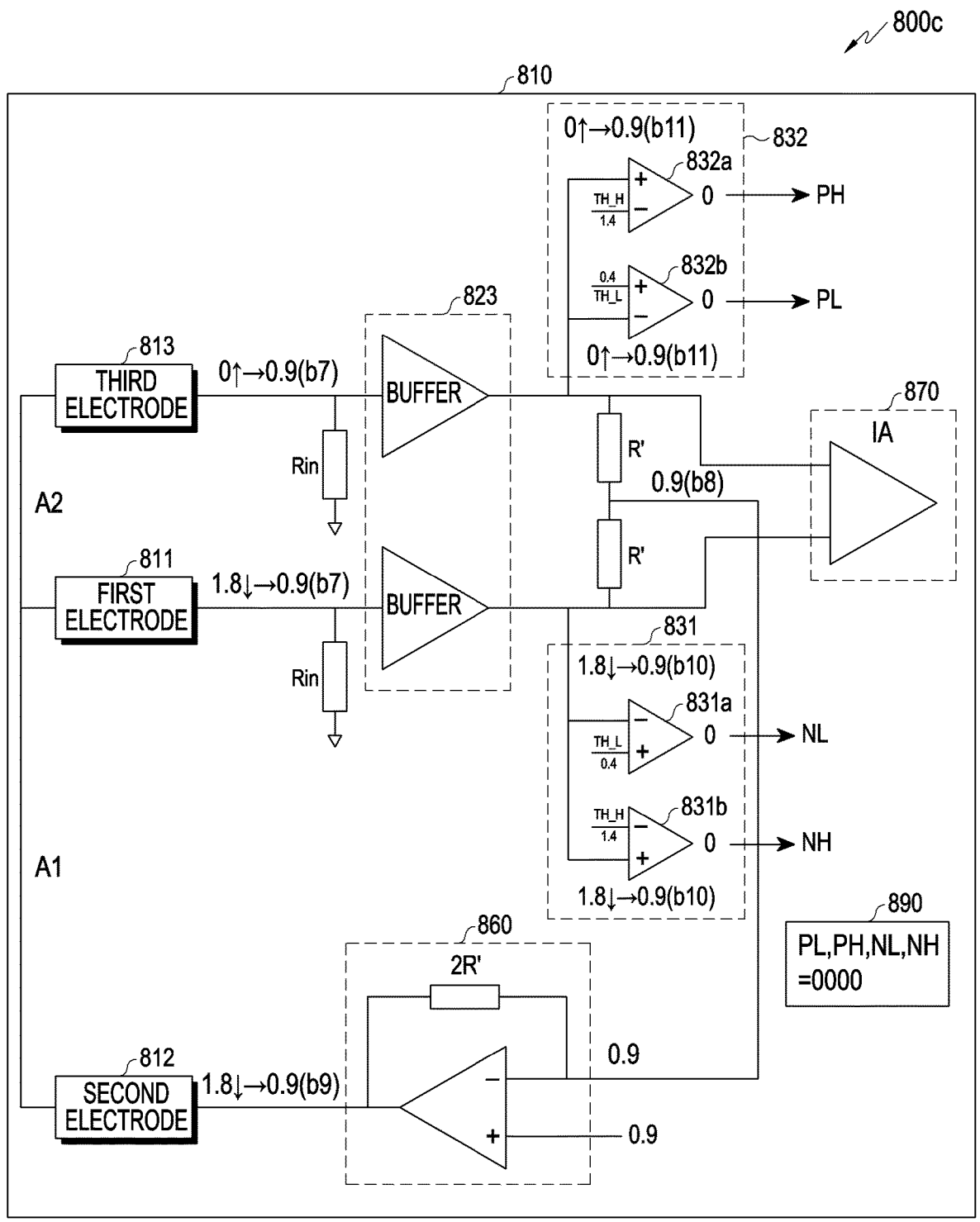

FIGS. 8A, 8B, and 8C are views 800a to 800c illustrating an example of detecting living body contact by a wearable electronic device according to an embodiment. FIGS. 8A to 8C are views illustrating the biometric signal measurement-capable state in the wearable electronic device and show the process from the time when the wearable electronic device contacts the second portion (e.g., finger) of the living body, with the first portion (e.g., wrist) of the living body in contact with the wearable electronic device, to the final stable state in which information indicating contact of both the first portion (e.g., wrist) and second portion (e.g., finger) of the living body to the wearable electronic device may be output. FIGS. 8A to 8C illustrate the same living body contact detecting unit 810 as that of FIGS. 5 to 7, except that different reference numbers are used.

Referring to FIG. 8A, when the third electrode 813 contacts the second portion (e.g., finger) of the living body while the first information, "PL, PH, NL, NH=1001" (790) indicating that the wearable electronic device contacts the first portion (e.g., wrist) of the living body is output from the living body contact detecting unit 810, an additional path A2 may be formed between the second electrode 812 and the third electrode 813. When the additional path A2 is formed between the second electrode 812 and the third electrode 813, the voltage at the third electrode 813 may rise (b1) so that the voltage output to the second connection detecting unit 832 may go up (b2), and the average voltage of the first electrode 811 and the third electrode 813 at the inverting (−) terminal increases (b3) so that the output voltage of the bias unit 860 may drop (b4).

Referring to FIG. 8B, as the average voltage input to the inverting (−) terminal of the bias unit 860 rises, if the output voltage of the bias unit 860 decreases, the voltage applied from the second electrode 812 to the first electrode 811 may drop (b5) so that the voltage output from the first connection detecting unit 831 may decrease (b6).

Referring to FIGS. 8A and 8B, when the output value of the bias unit 860 is varied as the third electrode 813 contacts the second portion (e.g., finger) of the living body, with the first portion (e.g., wrist) of the living body simultaneously contacting the first electrode 811 and the second electrode 812, the average voltage between the first electrode 811 and the third electrode 813 input to the inverting (−) terminal of the bias unit 860 may be adjusted to a predetermined voltage (e.g., 0.9V) so that the same second voltage is applied from the second electrode 812 to each of the first electrode 811 and the third electrode 813 as shown in FIG. 8C. When the average voltage is adjusted to the predetermined voltage (e.g., 0.9V), the second voltage applied to the first electrode 811 and the third electrode 813 may become 0.4V to 1.4V.

Referring to FIG. 8C, the voltage at the first electrode 811 may be decreased to a target voltage (e.g., 0.9V), and the voltage at the third electrode 813 may be increased to the target voltage (e.g., 0.9V) (b7) so that the average voltage may be adjusted to the predetermined voltage (e.g., 0.9V) (b8). When the average voltage (e.g., 0.9V) adjusted to the predetermined voltage is input to the inverting (−) terminal of the bias unit 860, the bias unit 860 may output the target voltage (e.g., 0.9V) (b9). As the second electrode 812 applies the second voltage (e.g., 0.9V) to each of the first electrode 811 and the third electrode 813, the second voltage (e.g., 0.9V) may be output to the first connection detecting unit 831 and the second connection detecting unit 832.

The second voltage (e.g., 0.9V) which is input to each of the first comparator 831a and the second comparator 831b included in the first connection detecting unit 831 may be compared with the first reference voltage (TH_L=0.4V, TH_H=1.4V), and "NL=0, NH=0," as information according to the result of comparison, may be output (b10). The second voltage (e.g., 0.9V) which is input to each of the first comparator 832a and the second comparator 832b included in the second connection detecting unit 832 may be compared with the second reference voltage (TH_H=1.4V, TH_L=0.4V), and the output of "PL=0, PH=0," which is the information according to the result of comparison, may be maintained. "PL, PH, NL, NH=0000" (890), which is the second information resultant from summating the information (PL, PH) output from the second connection detecting unit 832 and the information (NL, NH) output from the first connection detecting unit 831 and listing the pieces of information in order, may be output to the processor (e.g., the processor 220 of FIG. 2). The processor may detect that the operation state for biometric signal measurement of the wearable electronic device is the biometric signal measurement-capable state, based on the second information "PL, PH, NL, NH=0000" (890) output from the living body contact detecting unit 810.

According to an embodiment, a wearable electronic device (e.g., the wearable electronic device 201 of FIG. 2) comprises at least two electrodes (e.g., the first electrode 312 and third electrode 313 of FIG. 3) for measuring a biometric signal, a living body contact detecting unit (e.g., the living body contact detecting unit 215 of FIG. 2 or the living body contact detecting unit 310 of FIG. 3) configured to apply a voltage to at least one electrode contacting a living body among the at least two electrodes and output information indicating an operation state for biometric signal measurement of the wearable electronic device based on a voltage output from the at least one electrode, and a processor (e.g., the processor 120 of FIG. 1A or the processor 220 of FIG. 2) configured to determine the operation state for biometric signal measurement of the wearable electronic device, based on the information received from the living body contact detecting unit.

According to an embodiment, the living body contact detecting unit (e.g., the living body contact detecting unit 310 of FIG. 3) is configured to, when a first electrode (e.g., the first electrode 311 of FIG. 3) among the at least two electrodes for biometric signal measurement contacts first portion of the living body, apply a first voltage to the first electrode and, when the first electrode and a third electrode (e.g., the third electrode 313 of FIG. 3), among the at least two electrodes contact the first portion of the living body and a second portion of the living body, respectively, apply a second voltage different from the first voltage to each of the first electrode and the third electrode.

According to an embodiment, the living body contact detecting unit (e.g., the living body contact detecting unit 310 of FIG. 3) is configured to, when a first electrode for the biometric signal measurement and a second electrode for applying a voltage contact a first portion of the living body, output first information indicating that the operation state of the wearable electronic device is a biometric signal measurement-ready state, based on a first voltage applied to the first electrode; and when a third electrode for the biometric signal measurement contacts a second portion of the living body while the first information is output, output second information indicating that the operation state of the wearable electronic device is a biometric signal measurement-capable state, based on a second voltage applied to each of the first electrode and the third electrode.

According to an embodiment, the living body contact detecting unit (e.g., the living body contact detecting unit 310 of FIG. 3) is configured to, when the first electrode and the third electrode contact no portion of the living body, output third information indicating that the operation state of the wearable electronic device is a biometric signal measurement-stopped state, based on no voltage output from the third electrode and the first electrode.

According to an embodiment, the living body contact detecting unit (e.g., the living body contact detecting unit 310 of FIG. 3) includes the at least two electrodes including a first electrode (e.g., the first electrode 311 of FIG. 3) and a third electrode (e.g., the third electrode 313 of FIG. 3) for biometric signal measurement and a second electrode (e.g., the second electrode of FIG. 2) for applying a voltage to the first electrode and the third electrode, an electrode connection detecting unit (e.g., the electrode connection detecting unit 330 of FIG. 3) configured to output first information indicating that the operation state of the wearable electronic device is a biometric signal measurement-ready state based on a first voltage output from the first electrode and output second information indicating that the operation state of the wearable electronic device is a biometric signal measurement-capable state based on a second voltage output from the third electrode, a bias unit (e.g., the bias unit 350 of FIG. 3) configured to adjust a voltage to be applied from the second electrode to the first electrode and/or the third electrode to the first voltage and/or the second voltage, and a measuring unit (e.g., the measuring unit 370 of FIG. 3) configured to measure the biometric signal using one or more differences between potential values measured at the first electrode and the third electrode.

According to an embodiment, the electrode connection detecting unit (e.g., the electrode connection detecting unit 330 of FIG. 3) includes a first connection detecting unit (e.g., the first connection detecting unit 331 of FIG. 3) configured to compare a first reference voltage with the first voltage and/or the second voltage output from the first electrode and a second connection detecting unit (e.g., the second connection detecting unit 332 of FIG. 3) configured to compare a second reference voltage with the second voltage output from the third electrode.

According to an embodiment, among the at least two electrodes, a first electrode and a second electrode is placed in positions of the wearable electronic device, where the first electrode and the second electrode can contact a first portion of the living body and, among the at least two electrodes, a third electrode can contact a second portion of the living body in a position different from the positions of the first electrode and the second electrode.

According to an embodiment, the wearable electronic device further comprises a memory configured to store biometric information and a display displaying the biometric information.

According to an embodiment, the processor is configured to, upon receiving first information indicating that the operation state of the wearable electronic device is a biometric signal measurement-ready state, switch to the biometric signal measurement-ready state, maintain a session for the biometric signal measurement-ready state and, upon receiving second information indicating that the operation state of the wearable electronic device is a biometric signal measurement-capable state while maintaining the session for the biometric signal measurement-ready state, automatically switch to the biometric signal measurement-capable state to measure the biometric signal.

According to an embodiment, the processor is configured to, upon receiving first information indicating that the operation state of the wearable electronic device is a biometric signal measurement-ready state, display information related to the biometric signal measurement-ready state of the wearable electronic device on a user interface (UI) and, upon receiving second information indicating that the operation state of the wearable electronic device is a biometric signal measurement-capable state while displaying the information related to the biometric signal measurement-ready state on the UI, display information related to the biometric signal measurement-capable state of the wearable electronic device on the UI.

According to an embodiment, the processor is configured to, upon receiving third information indicating that the operation state of the wearable electronic device is a biometric signal measurement-stopped state, switch to the biometric signal measurement-stopped state.

Figure 9:
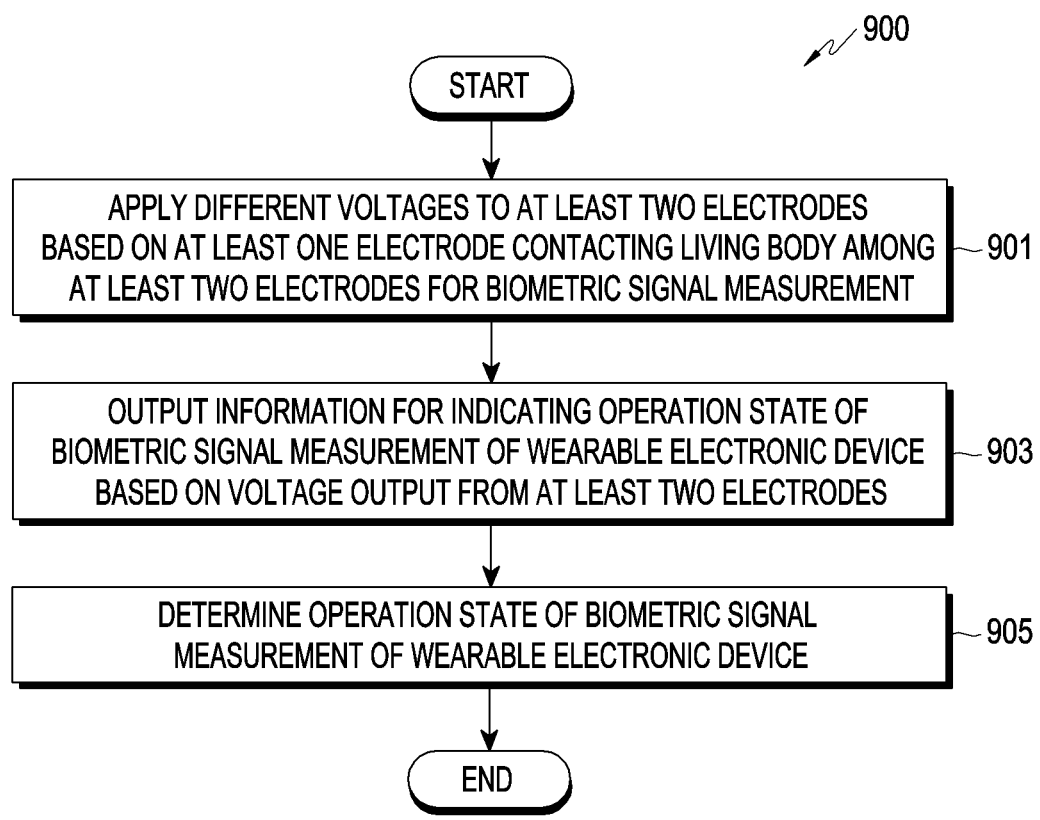
FIG. 9 is a flowchart illustrating an example of detecting living body contact by a wearable electronic device according to an embodiment.

FIG. 9 is a flowchart 900 illustrating an example of detecting living body contact by a wearable electronic device according to an embodiment. The living body contact detecting operations may include operations 901 to 905. The living body contact detecting operations may be performed by a wearable electronic device (e.g., the electronic device 101 of FIG. 1), at least one processor (e.g., the processor 120 of FIG. 1A) of the electronic device, the wearable electronic device 201 of FIG. 2, or the processor (e.g., the processor 220 of FIG. 2 and/or the living body contact detecting unit 215 of FIG. 2) of the wearable electronic device. According to an embodiment, at least one of operations 901 to 905 may be omitted, or some operations may be performed in a different order, or other operations may be added.

Referring to FIG. 9, in operation 901, the wearable electronic device may apply different voltages to the at least two electrodes based on at least one electrode contacting the living body among at least two electrodes for biometric signal measurement.

According to an embodiment, when the first electrode (e.g., the first electrode 311 of FIG. 3) for biometric signal measurement and the second electrode (e.g., the second electrode 312 of FIG. 3) for applying voltage in the living body contact detecting unit (e.g., the living body contact detecting unit 310 of FIG. 3) contacts a first portion (e.g., wrist) of the living body, the second electrode may apply the first voltage (e.g., the maximum voltage, e.g., 1.8V) to the first electrode.

According to an embodiment, when the third electrode (e.g., the third electrode 313 of FIG. 3) for biometric signal measurement contacts a second portion (e.g., finger) of the living body while the first portion (e.g., wrist) of the living body is in contact with the first electrode (e.g., the first electrode 312 of FIG. 3) and the second electrode (e.g., the second electrode 313 of FIG. 3) in the living body contact detecting unit (e.g., the living body contact detecting unit 310 of FIG. 3), the second electrode may apply the second voltage (e.g., 0.9V), which is lower than the first voltage, to each of the first electrode and the third electrode.

In operation 903, the wearable electronic device may output information indicating the operation state of the biometric signal measurement of the wearable electronic device based on the voltage output from the at least two electrodes.

According to an embodiment, when the first electrode (e.g., the first electrode 311 of FIG. 3) for biometric signal measurement and the second electrode (e.g., the second electrode 312 of FIG. 3) for applying voltage in the living body contact detecting unit (e.g., the living body contact detecting unit 315 of FIG. 3) contacts the first portion (e.g., wrist) of the living body so that the second electrode applies the first voltage (e.g., the maximum voltage, e.g., 1.8V) to the first electrode, first information indicating that the operation state of the wearable electronic device is the biometric signal measurement-ready state may be output based on the first voltage.

According to an embodiment, when the third electrode (e.g., the third electrode 313 of FIG. 3) for biometric signal measurement contacts the second portion (e.g., finger) of the living body while the first portion (e.g., wrist) of the living body is in contact with the first electrode (e.g., the first electrode 312 of FIG. 3) and the second electrode (e.g., the second electrode 313 of FIG. 3) in the living body contact detecting unit (e.g., the living body contact detecting unit 310 of FIG. 3) so that the second electrode applies the second voltage (e.g., 0.9V) to each of the first electrode and the third electrode, second information indicating that the operation state of the wearable electronic device is the biometric signal measurement-capable state may be output based on the second voltage.

According to an embodiment, when the first electrode and the third electrode contact no portion of the living body while the second information is output from the living body contact detecting unit (e.g., the living body contact detecting unit 310 of FIG. 3), third information indicating that the wearable electronic device contacts no portion of the living body may be output based on the voltage (e.g., 0V) output from the first electrode and the third electrode to which no voltage is applied from the second electrode.

In operation 905, the wearable electronic device may determine the operation state for biometric signal measurement of the wearable electronic device based on the information indicating the operation state for biometric signal measurement of the wearable electronic device.

According to an embodiment, it may be determined that the operation state of the wearable electronic device is the biometric signal measurement-ready state, based on the first information output from the living body contact detecting unit (e.g., the living body contact detecting unit 310 of FIG. 3).

According to an embodiment, it may be determined that the operation state of the wearable electronic device is the biometric signal measurement-capable state, based on the second information output from the living body contact detecting unit (e.g., the living body contact detecting unit 310 of FIG. 3).

According to an embodiment, it may be determined that the operation state of the wearable electronic device is the biometric signal measurement-stopped state, based on the third information output from the living body contact detecting unit (e.g., the living body contact detecting unit 310 of FIG. 3).

Figure 10:
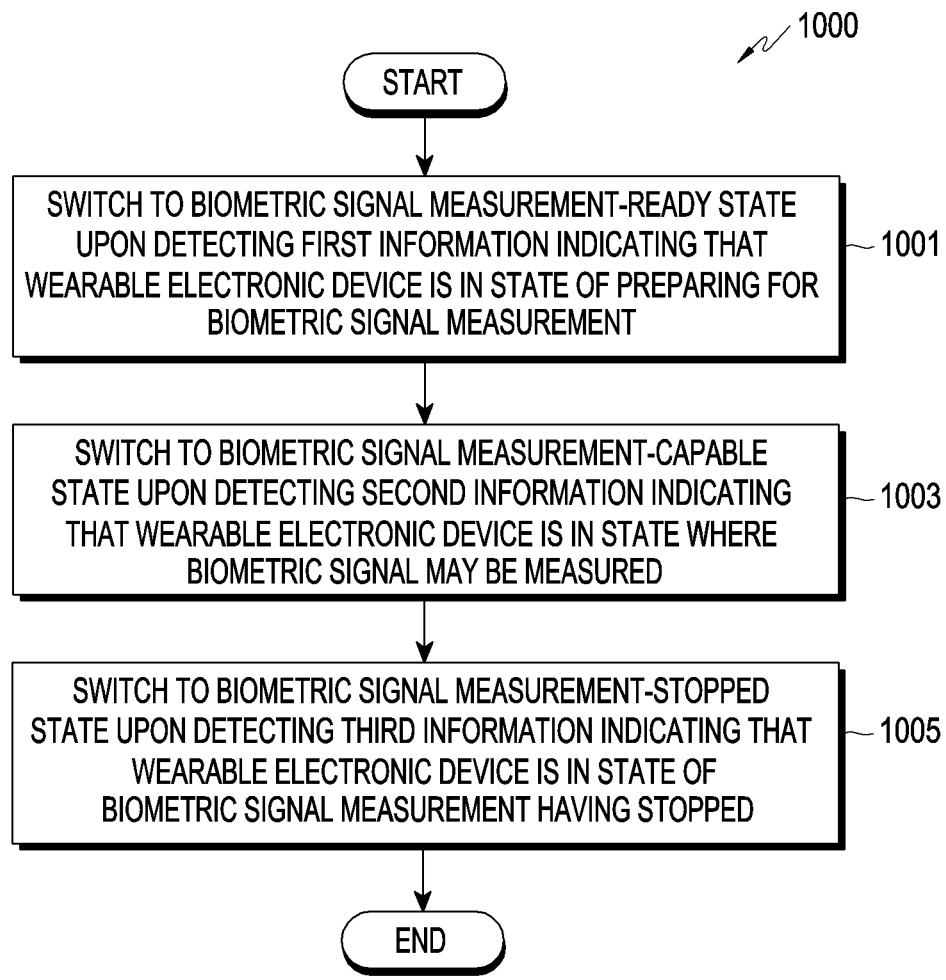
FIG. 10 is a flowchart illustrating an example of detecting living body contact by a wearable electronic device according to an embodiment.

FIG. 10 is a flowchart 1000 illustrating an example of detecting living body contact by a wearable electronic device according to an embodiment. The living body contact detecting operations may include operations 1001 to 1005. The living body contact detecting operations may be performed by a wearable electronic device (e.g., the electronic device 101 of FIG. 1), at least one processor (e.g., the processor 120 of FIG. 1A) of the electronic device, the wearable electronic device 201 of FIG. 2, or the processor (e.g., the processor 220 of FIG. 2 and/or the living body contact detecting unit 215 of FIG. 2) of the wearable electronic device. According to an embodiment, at least one of operations 1001 to 1005 may be omitted, or some operations may be performed in a different order, or other operations may be added.

Referring to FIG. 10, in operation 1001, upon detecting first information indicating that the operation state for biometric signal measurement of the wearable electronic device is the biometric signal measurement-ready state as the wearable electronic device contacts the first portion (e.g., wrist) of the living body, the wearable electronic device may switch to the biometric signal measurement-ready state. According to an embodiment, upon receiving the first information (e.g., the first information (PL, PH, NL, NH=1001) (790) of FIG. 7D), the wearable electronic device may search for an application (e.g., ECG application) for biometric signal measurement and prepare to execute the application.

According to an embodiment, upon switching to the biometric signal measurement-ready state in response to reception of the first information (PL, PH, NL, NH=1001) (790) of FIG. 7D), the wearable electronic device may measure at least one of heartrate, oxygen saturation, blood pressure, stress level, or sleep information based on the signal received via the PPG sensor (e.g., 415 of FIG. 4A) mounted on the rear surface of the wearable electronic device in the biometric signal measurement-ready state and display information about at least one of the measured heartrate, oxygen saturation, blood pressure, stress level, or sleep information on the display (e.g., the display 260 of FIG. 2).

According to an embodiment, the wearable electronic device may switch to the biometric signal measurement-ready state based on living body approaching information detected by the PPG sensor and the information (PL, PH, NL, NH=1001) (790) of FIG. 7D) detected by the electrodes. In the case where the living body approaching information is detected using the PPG sensor alone, a predetermined number of samples or more may be needed, so that it may take time to determine the biometric signal measurement-ready state. Thus, when the electrodes are used together with the PPG sensor, it may be quickly determined whether it is in the biometric signal measurement-ready state. When the wearable electronic device has difficulty in judging contact of the living body, such as when the user wears the wearable electronic device with a shirt in-between, the user's skin is dry, the ambient temperature is low, or the user's arm is hairy, it may be quickly and precisely determined whether it is in the biometric signal measurement-ready state by using the PPG sensor along with the electrodes.

In operation 1003, upon detecting second information indicating that the operation state for biometric signal measurement of the wearable electronic device is the biometric signal measurement-capable state as the first portion (e.g., wrist) of the living body and the second portion (e.g., finger) of the living body contact the wearable electronic device, the wearable electronic device may switch to the biometric signal measurement-capable state.

According to an embodiment, upon receiving the second information (e.g., the second information (PL, PH, NL, NH=0000)(890) of FIG. 8C), the wearable electronic device may execute an application (e.g., ECG application) for biometric signal measurement, receive the biometric signal measured from the measuring unit (e.g., the measuring unit 370 of FIG. 3) of the living body contact detecting unit (e.g., the living body contact detecting unit 310 of FIG. 3), and display information about the biometric signal on the display (e.g., the display 260 of FIG. 2).

In operation 1005, upon detecting third information (e.g., the third information (PL, PH, NL, NH=1010)(690) of FIG. 6) indicating that the operation state for biometric signal measurement of the wearable electronic device is the biometric signal measurement-stopped state as the wearable electronic device contacts no portion of the living body, the wearable electronic device may switch to the biometric signal measurement-stopped state. According to an embodiment, in this state, the contact, to the wearable electronic device, of the first portion (e.g., wrist) of the living body and the second portion (e.g., finger) of the living body is released. Thus, the third information may be information indicating the release of the contact of the first portion (e.g., wrist) of the living body and/or the second portion (e.g., finger) of the living body.

According to an embodiment, the wearable electronic device may switch to the biometric signal measurement-stopped state based on living body approaching information detected by the PPG sensor and the information (e.g., the third information (PL, PH, NL, NH=(PL, PH, NL, NH=1010) (690) of FIG. 6) detected by the electrodes.

In the case where the living body approaching information is detected using the PPG sensor alone, a predetermined number of samples or more may be needed, so that it may take time to determine the biometric signal measurement-stopped state. Thus, when the electrodes, which may immediately detect contact and/or non-contact of the living body, are used together with the PPG sensor, it may be quickly determined whether it is in the biometric signal measurement-stopped state. When the electrodes are used, a DC-based method is used, rather than an AC-based method which is poor at detecting the contact or non-contact of the first portion and second portion of the living body to the wearable electronic device, due to a path formed between the two electrodes which are supposed to be electrically insulated from each other. When the electrodes are used by the DC-based method, no additional noise may be caused unlike in the AC-based method which applies an alternating current.

As the wearable electronic device precisely determines contact or non-contact to portions (e.g., the first portion and the second portion) of the living body as shown in FIG. 10, it may aid in precisely determining the user's context, thereby increasing the reliability of user authentication and payment service. As the wearable electronic device quickly determines the contact and non-contact to the portion (e.g., the first portion and second portion) of the living body based on the approaching information from the PPG sensor and the information from the electrodes, it may be possible to determine the context in an complementary manner (e.g. complementary to the PPG sensor) even when a temporary non-contact occurs to the body portion (e.g., the first portion and second portion), leading to better usability.

Figure 11:
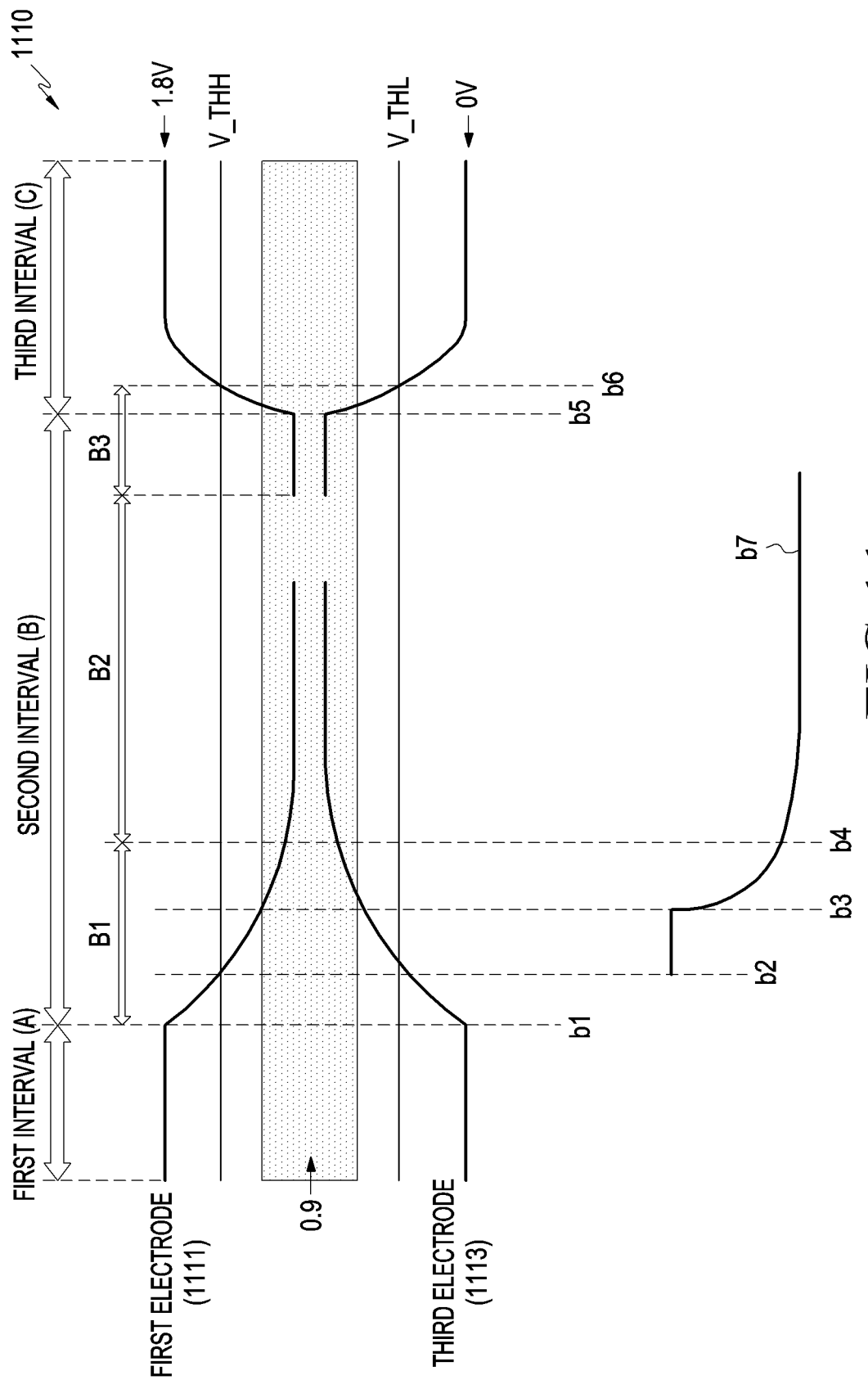
FIG. 11 is a flowchart illustrating an example of detecting a biometric signal by a wearable electronic device according to an embodiment.

FIG. 11 is a flowchart 1110 illustrating an example of detecting a biometric signal by a wearable electronic device according to an embodiment.

FIG. 11 illustrates a first interval A in which the wearable electronic device (e.g., the wearable electronic device 201 of FIG. 2) is worn on the user's wrist and is in the biometric signal measurement-ready state, a second interval B in which while the first interval A is maintained, a finger contacts the third electrode of the wearable electronic device so that the biometric signal is automatically measured, and a third interval C in which contact of a finger to the third electrode of the wearable electronic device is not detected.

In the first interval A, the wearable electronic device (e.g., the wearable electronic device 201 of FIG. 2) is worn on the first portion (e.g., wrist) of the living body, and the wearable electronic device is currently in the biometric signal measurement-ready state. In the first interval A, as the first electrode 1111 (e.g., the first electrode 711 of FIGS. 7A to 7D) contacts the first portion (e.g., wrist) of the living body, the first electrode 1111 outputs the maximum voltage, e.g., 1.8V, which is applied from the second electrode (e.g., the second electrode 712 of FIGS. 7A to 7D) which, together with the first electrode 1111, forms a path, and the third electrode 1113 (e.g., the third electrode 713 of FIGS. 7A to 7D) which the living body does not contact may output 0V. As the first electrode 1111 outputs the maximum voltage, 1.8V, and the third electrode 1113 outputs 0V in the first interval A, the wearable electronic device (e.g., the living body contact detecting unit 215 of FIG. 3) may output first information (e.g., PL, PH, NL, NH=1001) indicating the biometric signal measurement-ready state.

In the second interval B, the third electrode 1113 (e.g., the third electrode 813 of FIGS. 8A to 8C) contacts the second portion (e.g., finger) of the living body while the first interval A, where the wearable electronic device is worn on the first portion (e.g., wrist) of the living body, is maintained. In response to contact of the second portion (e.g., finger) of the living body to the third electrode 1113, the wearable electronic device may automatically measure the biometric signal.

The second interval B may include an initial stabilization interval B1, a biometric signal measurement interval B2, and a biometric signal measurement termination interval B3.

The initial stabilization interval B1 may include a first time b1, a second time b2, a third time b3, and a fourth time b4 and may include a predetermined time interval (e.g., 1 second) or less.

The first time b1 is the time when the second portion (e.g., finger) of the living body actually contacts the third electrode 1113, with the wearable electronic device worn on the first portion (e.g., wrist) of the living body.

The second time b2, which may occur a predetermined time interval (e.g., 10 ms or less) after the first time b1, is the time when the wearable electronic device detects the contact of the second portion (e.g., finger) of the living body to the third electrode 1113, with the wearable electronic device worn on the first portion (e.g., wrist) of the living body. As the first electrode 1111 (e.g., the first electrode 811 of FIGS. 8A to 8C) contacts the first portion (e.g., wrist) of the living body, and the third electrode 1113 contacts the second portion (e.g., finger) of the living body, the first electrode 1111 and the third electrode 1113 may output the voltage which is applied from the second electrode which forms paths with each of the first electrode 1111 and the third electrode 1113. The interval between the first time b1 and the second time b2 is a stabilization interval for outputting a target voltage (e.g., 0.9V) to each of the first electrode 1111 and the third electrode 1113 from the second electrode. Thus, at the second time b2, the second electrode outputs the target voltage (e.g., 0.9V) to each of the first electrode 1111 and the third electrode 1113, so that the second information (e.g., PL, PH, NL, NH=0000) indicating that the wearable electronic device is in the biometric signal measurement-capable state may be output. At the second time b2, a preparation signal for biometric signal measurement may be transferred to the measuring unit (e.g., the measuring unit 370 of FIG. 3) of the biometric signal detecting unit that measures the biometric signal.

The third time b3 is the time when the biometric signal may be measured, and the interval between the second time b2 and the third time b3 may be referred to as a signal saturation interval.

The fourth time b4 is the time when valid signal values for biometric signal measurement may be gathered. During the interval (e.g., 10 ms) between the third time b3 and the fourth time b4, excessive response signal values received as the voltage value is varied may be disregarded and, from the fourth time b4, stable and effective signal values for biometric signal measurement may be obtained.

In the interval B2 for gathering signals for biometric signal measurement, stable and effective signal values b7 for biometric signal measurement may be received during a predetermined time interval (e.g., 30 ms) and the biometric signal may be measured. During the interval B2 for gathering signals for biometric signal measurement, the measuring unit (e.g., the measuring unit 370 of FIG. 3) may measure the biometric signal using the difference between the voltages at the first electrode 1111 and the third electrode 1113, based on the effective signal values for biometric signal measurement, received during the predetermined time (e.g., 30 ms).

The biometric signal measurement termination interval B3 may include a fifth time b5 which is the time when the contact of the second portion (e.g., finger) of the living body to the third electrode 1113 is substantially released while the wearable electronic device stays worn on the first portion (e.g., wrist) of the living body and a sixth time b6 which is the time when the wearable electronic device detects the release of the contact of the second portion (e.g., finger) of the living body to the third electrode 1111 while the wearable electronic device stays worn on the first portion (e.g., wrist) of the living body.

The third interval C is an interval during which the wearable electronic device is currently in the biometric signal measurement-ready state as the contact of the second portion (e.g., finger) of the living body to the third electrode 1113 (e.g., the third electrode 713 of FIGS. 7A to 7D) is released, with the wearable electronic device worn on the first portion (e.g., wrist) of the living body. In the third interval C, as in the first interval A, the wearable electronic device (e.g., the living body contact detecting unit 215 of FIG. 3) may output the first information (e.g., PL, PH, NL, NH=1001) indicating the biometric signal measurement-ready state.

Figure 12A:
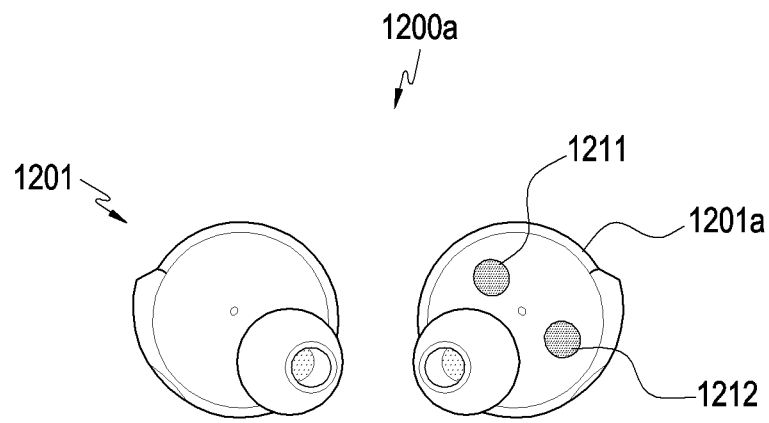
FIG. 12A is a front perspective view illustrating a wearable electronic device according to an embodiment.
Figure 12B:
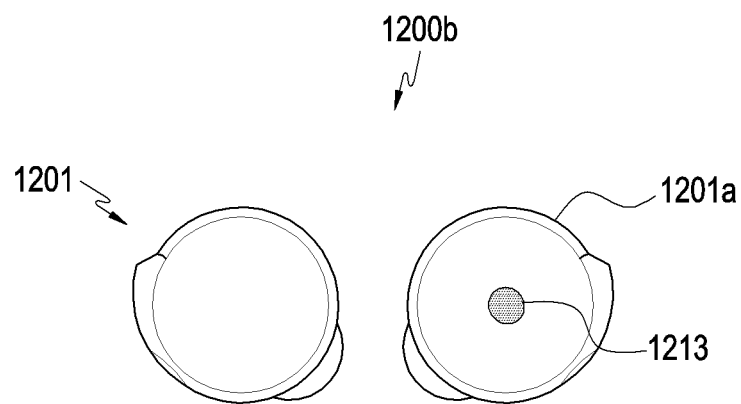
FIG. 12B is a rear perspective view illustrating a wearable electronic device as shown in FIG. 12A.

FIG. 12A is a front perspective view 1200a illustrating a wearable electronic device according to an embodiment. FIG. 12B is a rear perspective view 1200b illustrating the wearable electronic device of FIG. 12A.

Referring to FIGS. 12A and 12B, a pair of earbuds 1201, which is the wearable electronic device, may include one earbud 1201a. The one earbud 1201a may include a plurality of electrodes 1211, 1212, and 1213 for detecting biometric signals. The plurality of electrodes may include a first electrode 1211 (e.g., the first electrode 311 of FIG. 3) and a third electrode 1213 (e.g., the third electrode 313 of FIG. 3) for biometric signal measurement and a second electrode 1212 (e.g., the second electrode 312 of FIG. 3) for applying voltage to the first electrode 1211 and/or the third electrode 1213. The earbud 1201 may include the configuration of FIGS. 2 and 3.

When the pair of earbuds 1201 or one earbud 1201a of the pair 1201 is inserted to the user's ear, the first electrode 1211 and the second electrode 1212 positioned on the same surface of the earbud 1201a contact a first portion (e.g., ear) of the living body, a path may be formed between the first electrode 1211 and the second electrode 1212. And, as the first electrode 1211 outputs the voltage which is applied from the second electrode 1212, the earbud pair 1201 may turn into the biometric signal measurement-ready state. While the earbud pair 1201 remains in the biometric signal measurement-ready state, if the third electrode 1213 contacts a second portion (e.g., finger) of the living body, an additional path may be formed between the second electrode 1212 and the third electrode 1213, and the first electrode 1211 and the third electrode 1213 each may output the voltage which is applied from the second electrode 1212, so that the earbud pair 1201 may automatically measure the biometric signal. The result of biometric signal measurement may be output via the electronic device communicating with the earbud pair 1210.

Although the wearable electronic device is exemplified as a watch as shown in FIGS. 1B to 1D and 4A to 4D and as earbuds as shown in FIGS. 12A and 12B, embodiments of the disclosure may also apply to other embodiments such as glasses which are worn on the user's face and contact the living body.

The watch, as the wearable electronic device, may also be worn on the user's ankle, not only on the user's wrist, and may detect living body contact and measuring biometric signals in the same manner.

According to an embodiment, a method for detecting contact of a living body to a wearable electronic device (e.g., the wearable electronic device 201 of FIG. 2) can comprise applying a voltage to at least one electrode contacting the living body among at least two electrodes for biometric signal measurement, outputting information indicating an operation state for biometric signal measurement of the wearable electronic device based on another voltage output from the at least one electrode, and determining the operation state of the biometric signal measurement of the wearable electronic device based on the information indicating the operation state of the biometric signal measurement of the wearable electronic device.

According to an embodiment, applying the voltage include, when a first electrode among the at least two electrodes for biometric signal measurement contacts a first portion of the living body, applying a first voltage to the first electrode and, when the first electrode and a third electrode, among the at least two electrodes contact the first portion of the living body and a second portion of the living body, respectively, applying a second voltage, different from the first voltage, to each of the first electrode and the third electrode.

According to an embodiment, outputting the information include, when a first electrode for the biometric signal measurement and a second electrode for applying the voltage contact a first portion of the living body, outputting first information indicating that the operation state of the wearable electronic device is a biometric signal measurement-ready state, based on a first voltage applied to the first electrode and, when a third electrode for the biometric signal measurement contacts a second portion of the living body while the first information is output, outputting second information indicating that the operation state of the wearable electronic device is a biometric signal measurement-capable state, based on a second voltage applied to each of the first electrode and the third electrode.

According to an embodiment, the method further comprises, when the first electrode and the third electrode contact no portion of the living body, outputting third information indicating that the operation state of the wearable electronic device is a biometric signal measurement-stopped state, based on no voltage output from the third electrode and the first electrode.

According to an embodiment, among the at least two electrodes, a first electrode and a second electrode are be placed in positions of the wearable electronic device, where the first electrode and the second electrode can contact a first portion of the living body.

According to an embodiment, among the at least two electrodes, a third electrode can contact a second portion of the living body in a position different from the positions of the first electrode and the second electrode.

According to an embodiment, the method further comprise, upon receiving first information indicating that the operation state of the wearable electronic device is a biometric signal measurement-ready state, switching to the biometric signal measurement-ready state, maintaining a session for the biometric signal measurement-ready state and, upon receiving second information indicating that the operation state of the wearable electronic device is a biometric signal measurement-capable state while maintaining the session for the biometric signal measurement-ready state, automatically switching to the biometric signal measurement-capable state to measure the biometric signal.

According to an embodiment, the method further comprise, upon receiving first information indicating that the operation state of the wearable electronic device is a biometric signal measurement-ready state, displaying information related to the biometric signal measurement-ready state of the wearable electronic device on a user interface (UI) and, upon receiving second information indicating that the operation state of the wearable electronic device is a biometric signal measurement-capable state while displaying the information related to the biometric signal measurement-ready state on the UI, displaying information related to the biometric signal measurement-capable state of the wearable electronic device on the UI.

According to an embodiment, the method further comprise, upon receiving third information indicating that the operation state of the wearable electronic device is a biometric signal measurement-stopped state, switching to the biometric signal measurement-stopped state.

The electronic device according to various embodiments may be one of various types of electronic devices. The electronic devices may include, for example, a portable communication device (e.g., a smart phone), a computer device, a portable multimedia device, a portable medical device, a camera, a wearable device, or a home appliance. According to an embodiment of the disclosure, the electronic devices are not limited to those described above.

It should be appreciated that various embodiments of the disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a compiler or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program products may be traded as commodities between sellers and buyers. The computer program product may be distributed in the form of a machine-readable storage medium (e.g., compact disc read only memory (CD-ROM)), or be distributed (e.g., downloaded or uploaded) online via an application store (e.g., Play Store™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration.

According to various embodiments, operations performed by the module, the program, or another component may be carried out sequentially, in parallel, repeatedly, or heuristically, or one or more of the operations may be executed in a different order or omitted, or one or more other operations may be added.

There may be provided a storage medium storing instructions configured to, when executed by at least one processor, enable the at least one processor to perform operations such as applying a voltage to at least one electrode contacting the living body among at least two electrodes for biometric signal measurement, outputting information indicating an operation state for biometric signal measurement of the wearable electronic device based on another voltage output from the at least one electrode, and determining the operation state of the biometric signal measurement of the wearable electronic device based on the information indicating the operation state of the biometric signal measurement of the wearable electronic device.

As is apparent from the foregoing description, according to certain embodiments, a buffer having high input impedance is used, so that the bias unit, which is a voltage source, may operate at very low output current. Further, as compared with the conventional operation method in which voltage is measured by applying current, it is possible to prolong the battery life of the wearable electronic device. Since no current is applied between the two electrodes in certain situations, no additional noise (IR voltage drop by current*contact resistance) occurs. It is also possible to measure the biometric signal while simultaneously detecting contact of a body portion to the wearable electronic device using the two electrodes.

The embodiments herein are provided merely for better understanding of the disclosure, and the disclosure should not be limited thereto or thereby. It should be appreciated by one of ordinary skill in the art that various changes in form or detail may be made to the embodiments without departing from the scope of the disclosure defined by the following claims.

Certain of the above-described embodiments of the present disclosure can be implemented in hardware, firmware or via the execution of software or computer code that can be stored in a recording medium such as a CD ROM, a Digital Versatile Disc (DVD), a magnetic tape, a RAM, a floppy disk, a hard disk, or a magneto-optical disk or computer code downloaded over a network originally stored on a remote recording medium or a non-transitory machine readable medium and to be stored on a local recording medium, so that the methods described herein can be rendered via such software that is stored on the recording medium using a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein.

What is claimed is:

1. A wearable electronic device, comprising:
a first electrode, a second electrode and a third electrode;
first circuitry including bias circuitry and electrode connection detecting circuitry; and
a processor configured to determine an operation state of the wearable electronic device for biometric signal measurement based on a first or a second operation state information received from the first circuitry,
wherein the first circuitry is configured to:
for detecting that the first electrode contacts a first portion of a living body without any contact between the living body and the third electrode:
output, via the bias circuitry, a first voltage to the second electrode for application of the first voltage to the first electrode,
compare a first reference voltage with the first voltage output from the first electrode, thereby resulting in a first comparison result, and
output, via the electrode connection detecting circuitry, the first operation state information indicating that the first electrode contacts the first portion of the living body without any contact between the living body and the third electrode, based on the first comparison result; and
for detecting that the third electrode contacts a second portion of the living body while the first electrode contacts the first portion of the living body:
output, via the bias circuitry, a second voltage to the second electrode for application of the second voltage to the first electrode and for application of the second voltage to the third electrode,
compare the first reference voltage with the second voltage output from the first electrode, thereby resulting in a second comparison result,
compare a second reference voltage with the second voltage output from the third electrode, thereby resulting in a third comparison result, and
output, via the electrode connection detecting circuitry, the second operation state information indicating that the third electrode contacts a second portion of the living body while the first electrode contacts the first portion of the living body, based on the second comparison result, and the third comparison result.

2. The wearable electronic device of claim 1,
wherein the first circuitry obtains first biometric signal for measuring a heartrate, and a second biometric signal that is an electrocardiogram.

3. The wearable electronic device of claim 2, wherein the first circuitry is configured to, when the first electrode and the third electrode contact no portion of the living body, output, to the processor, a third operation state information indicating that the operation state of the wearable electronic device is a biometric signal measurement-stopped state, based on no voltage output from the third electrode and the first electrode.

4. The wearable electronic device of claim 1, wherein the first circuitry further comprises:
a measuring circuitry configured to measure a biometric signal using one or more differences between potential values measured at the first electrode and the third electrode.

5. The wearable electronic device of claim 4, wherein the electrode connection detecting circuitry includes:
first connection detecting circuitry configured to provide the first comparison result or to provide the second comparison result; and
second connection detecting circuitry configured to provide the third comparison result.

6. The wearable electronic device of claim 1, wherein the first electrode and the second electrode are placed in positions of the wearable electronic device, wherein the first electrode and the second electrode are configured to contact the first portion of the living body, and
wherein the third electrode is configured to contact the second portion of the living body in a position different from the positions of the first electrode and the second electrode.

7. The wearable electronic device of claim 1, further comprising:
a memory configured to store biometric information; and
a display configured to display the biometric information.

8. The wearable electronic device of claim 1, wherein the processor is configured to:
upon receiving the first operation state information, switch to a biometric signal measurement-ready state;
maintain a session for the biometric signal measurement-ready state; and
upon receiving the second operation state information while maintaining the session for the biometric signal measurement-ready state, automatically switch to a biometric signal measurement-capable state to measure a biometric signal.

9. The wearable electronic device of claim 1, wherein the processor is configured to:
upon receiving the first operation state information, display first visual information related to a biometric signal measurement-ready state of the wearable electronic device, via a user interface (UI); and
upon receiving the second operation state information while displaying the first visual information related to the biometric signal measurement-ready state via the UI, display second visual information related to a biometric signal measurement-capable state of the wearable electronic device via the UI.

10. The wearable electronic device of claim 1, wherein the processor is configured to, upon receiving a third operation state information indicating that the operation state of the wearable electronic device is a biometric signal measurement-stopped state, switch to the biometric signal measurement-stopped state.

11. A method for detecting contact of a living body to a wearable electronic device including a first electrode, a second electrode and a third electrode, the method comprising:
for detecting that the first electrode contacts a first portion of the living body without any contact between the living body and the third electrode:
outputting a first voltage to the second electrode for application of the first voltage to the first electrode,
comparing a first reference voltage with the first voltage output from the first electrode, thereby resulting in a first comparison result, and
outputting a first operation state information indicating that the first electrode contacts the first portion of a living body without any contact between the living body and the third electrode, based on the first comparison result;
for detecting that the third electrode contacts a second portion of the living body while the first electrode contacts the first portion of the living body:
outputting a second voltage different from the first voltage to the second electrode for application of the second voltage to the first electrode and for application of the second voltage to the third electrode,
comparing the first reference voltage with the second voltage output from the first electrode, thereby resulting in a second comparison result,
comparing a second reference voltage with the second voltage output from the third electrode, thereby resulting in a third comparison result, and
outputting a second operation state information indicating that the third electrode contacts a second portion of the living body while the first electrode contacts the first portion of the living body, based on the second comparison result and the third comparison result; and
determining an operation state of the wearable electronic device for biometric signal measurement based on the first operation state information or the second operation state information.

12. The method of claim 11, further comprising:
obtaining a first biometric signal for measuring a heart rate, and a second biometric signal that is an electrocardiogram.

13. The method of claim 12, further comprising, when the first electrode and the third electrode contact no portion of the living body, outputting a third operation state information indicating that the operation state of the wearable electronic device is a biometric signal measurement-stopped state, based on no voltage output from the third electrode and the first electrode.

14. The method of claim 11, wherein the first electrode and the second electrode are placed in positions of the wearable electronic device, and wherein the first electrode and the second electrode are configured to contact the first portion of the living body.

15. The method of claim 14, wherein the third electrode is configured to contact a second portion of the living body in a position different from the positions of the first electrode and the second electrode.

16. The method of claim 11, further comprising:
upon receiving the first operation state information, switching to a biometric signal measurement-ready state;

maintaining a session for the biometric signal measurement-ready state; and upon receiving the second operation state information while maintaining the session for the biometric signal measurement-ready state, automatically switching to a biometric signal measurement-capable state to measure a biometric signal.

17. The method of claim 11, further comprising:

upon receiving the first operation state information, displaying first visual information related to a biometric signal measurement-ready state of the wearable electronic device, via a user interface (UI); and upon receiving the second operation state information while displaying the first visual information related to the biometric signal measurement-ready state via the UI, displaying second visual information related to a biometric signal measurement-capable state of the wearable electronic device via the UI.

18. The method of claim 11, further comprising, upon receiving a third operation state information indicating that the operation state of the wearable electronic device is a biometric signal measurement-stopped state, switching to the biometric signal measurement-stopped state.

* * * * *

UNITED STATES PATENT AND TRADEMARK OFFICE
CERTIFICATE OF CORRECTION

| | | |
|---|---|---|
| PATENT NO. | : 11,980,479 B2 | Page 1 of 1 |
| APPLICATION NO. | : 16/952168 | |
| DATED | : May 14, 2024 | |
| INVENTOR(S) | : Hyunjun Jung | |

It is certified that error appears in the above-identified patent and that said Letters Patent is hereby corrected as shown below:

In the Claims

Column 33, Claim 2, Line 7 should read as follows:
--measuring a heart rate, ...--

Signed and Sealed this
Twenty-third Day of July, 2024

Katherine Kelly Vidal
*Director of the United States Patent and Trademark Office*